United States Patent
Boyd et al.

(10) Patent No.: US 8,741,947 B2
(45) Date of Patent: Jun. 3, 2014

(54) BIOLOGICALLY ACTIVE MACROLIDES, COMPOSITIONS, AND USES THEREOF

(75) Inventors: Michael R. Boyd, Mobile, AL (US); Kirk R. Gustafson, Frederick, MD (US); Charles L. Cantrell, Longmont, CO (US)

(73) Assignee: The United States of America, as represented by the Secretary of the Department of Health and Human Services, Washington, DC (US)

( * ) Notice: Subject to any disclaimer, the term of this patent is extended or adjusted under 35 U.S.C. 154(b) by 541 days.

(21) Appl. No.: 12/851,691

(22) Filed: Aug. 6, 2010

(65) Prior Publication Data

US 2010/0298248 A1 Nov. 25, 2010

Related U.S. Application Data

(60) Continuation of application No. 11/435,189, filed on May 16, 2006, now Pat. No. 7,790,764, which is a division of application No. 10/333,710, filed as application No. PCT/US01/23633 on Jul. 24, 2001, now Pat. No. 7,144,918.

(60) Provisional application No. 60/220,270, filed on Jul. 24, 2000.

(51) Int. Cl.
*A01N 43/02* (2006.01)
*A61K 31/335* (2006.01)
*C07D 309/00* (2006.01)

(52) U.S. Cl.
USPC .......................................... 514/449; 549/356

(58) Field of Classification Search
USPC .......................................... 514/449; 549/356
See application file for complete search history.

(56) References Cited

FOREIGN PATENT DOCUMENTS

WO    WO 99 05136 A1   2/1999
WO    WO 00 51589 A2   9/2000

OTHER PUBLICATIONS

Pinedo et al., "Translational Research . . . ", The Oncologist 2000,, 5 (suppl1): 1-2 (www.The Oncologist .com).*
McMahon, Gerald, "VEGF Receptor Signaling in Tumor Angiogenesis", The Oncologist 2000; 5(suppl 1): 3-10 (www.The Oncologist.com).*
Boyd, "Some Practical Considerations and Applications of the National Cancer Institute In Vitro Anticancer Drug Discovery Screen," *Drug Development Research*, 34, 91-109 (1995).
Perry et al., "Okadaic Acid in New Zealand Sponges: Detection by Cytotoxicity, Protein Phosphatase Inhibition and Immunoassay Techniques," *Natural Product Letters*, 11(4), 305-312 (1998).
Cantrell et al., *J. Am. Chem. Soc.*, 122(347), 8825-8829 (2000).
Finbow et al., *Biochemical Journal*, 324, 697-712 (1997).
Gagliardi et al., *J. Med. Chem.*, 41(10), 1568-1573 (1998).
Gagliardi et al., *J. Med. Chem.*, 41(11), 1883-1893 (1998).
Pinedo et al., Translational Research . . . , The Oncologist 2000, 5 (suppl1): 1-2 (www.The Oncologist.com) 2000.
McMahon, "VEGF Receptor Signaling in Tumor Angiogenesis," *The Oncologist 2000*: 5 (*supp 1*): 3-10 (www.TheOncologist.com) 2000.
Rashid et al., *J. Nat. Prod.*, 64(10), 1341-1344 (2001).
Rashid et al., *Tetrahedron Letters*, 42, 1623-1626 (2001).

* cited by examiner

*Primary Examiner* — Paul V. Ward
(74) *Attorney, Agent, or Firm* — Leydig, Voit & Mayer, Ltd.

(57) ABSTRACT

The present invention provides a compound of the formula (I) or (II, wherein $R^1$ is H, alkyl, alkenyl or aryl, $R^2$ is H, alkyl or aryl, $R^3$ is H, a alkyl, alkenyl or aryl, $R^4$ and $R^4$-$R^8$ are independently $R^{10}$, $C(O)R^{10}$ or $SO_2R^{10}$, wherein $R^{10}$ is H, alkyl, alkenyl or aryl, and $R^9$ is $R^{9a}$, $C(O)R^{9a}$ or $SO_2R^{9a}$, wherein $R^{9a}$ is H, alkyl, alkenyl or aryl. $R^{9a}$ can be unsubstituted or substituted with one or more oxo(=O), $OR^{9b}$, $OC(O)R^{9b}$, $OSO_2R^{9b}$, $NHR^{9b}$, $NHC(O)R^{9b}$ and $NHSO_2R^{9b}$ groups. $R^{9b}$ is H, alkyl, alkenyl, or aryl. $R^{9b}$ can be unsubstituted or substituted with one or more groups such as oxo(=O), $OR^{9c}$, $CO_2R^{9c}$, $CO_2R^{9c}$ and $OC(O)R^{9c}$. $R^{9c}$ is H, or a unsubstituted or substituted alkyl, alkenyl or aryl. The present invention further provides a composition comprising at least one compound of the present invention and a pharmaceutically acceptable carrier, alone or in combination with at least one additional active agent. The present invention further provides a method of treating a condition treatable by the inhibition of vacuolar-type (H+)-ATPase and a method of treating cancer.

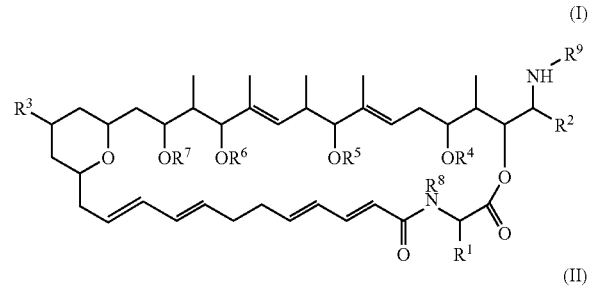

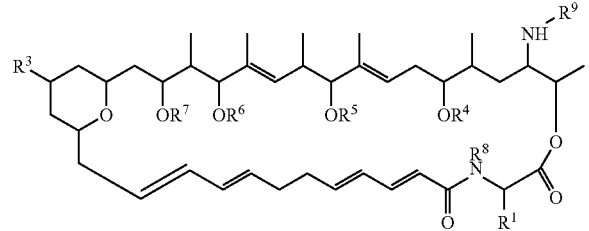

15 Claims, 5 Drawing Sheets

(1) $R^{1a}$ = H; $R^4$ =  ; $R^{9b}$ = OH; $R^{9c}$ = $CO_2CH_3$ (2) $R^{1a}$ = $R^4$ = H; $R^{9b}$ = OH; $R^{9c}$ = $CO_2CH_3$ (3) $R^{1a}$ = $CH_3$; $R^4$ =  ; $R^{9b}$ = OH; $R^{9c}$ = $CO_2CH_3$ (4) $R^{1a}$ = H; $R^4$ = $C(O)CH_2CH(OH)CO_2H$; $R^{9b}$ = H; $R^{9c}$ = $CO_2CH_3$ (5) $R^{1a}$ = $CH_3$; $R^4$ = $C(O)CH_2CH(OH)CO_2CH_3$; $R^{9b}$ = H; $R^{9c}$ = $CO_2CH_3$ (6) $R^{1a}$ = H; $R^4$ = $C(O)CH_2CH(OH)CO_2H$; $R^{9b}$ = $R^{9c}$ = H (7) $R^{1a}$ = $CH_3$; $R^4$ = $C(O)CH_2CH(OH)CO_2CH_3$; $R^{9b}$ = $R^{9c}$ = H (8) $R^{1a}$ = H; $R^4$ =  ; $R^{9b}$ = OH; $R^{9c}$ = $CO_2CH_3$ (9) $R^{1a}$ = $CH_3$; $R^4$ =  ; $R^{9b}$ = OH; $R^{9c}$ = $CO_2CH_3$

BIOLOGICALLY ACTIVE MACROLIDES, COMPOSITIONS, AND USES THEREOF

CROSS-REFERENCE TO RELATED APPLICATIONS

This patent application is continuation of U.S. patent application Ser. No. 11/435,189, filed May 16, 2006, which is a division of U.S. patent application Ser. No. 10/333,710, filed Jun. 11, 2003, now U.S. Pat. No. 7,144,918, which is a U.S. National Phase of International Patent Application No. PCT/US01/23633, filed Jul. 24, 2001, claiming the benefit of U.S. Provisional Patent Application No. 60/220,270, filed Jul. 24, 2000. The disclosures of the related applications are incorporated by reference.

TECHNICAL FIELD OF THE INVENTION

The present invention relates to vacuolar-type (H+)-ATPase-inhibiting macrocyclic compounds, compositions, and methods of using them.

BACKGROUND OF THE INVENTION

Vacuolar (or vacuolar-type or V-type) (H+)-ATPases have been described as "a universal proton pump of eukaryotes" (Finbour and Harrison, Biochem. J., 324, 697-712 (1997)). Vacuolar-type (H+)-ATPases are present in many tissues and cells of the body. Intracellular vacuolar (H+)-ATPase activities are present in certain organelles, and are responsible for maintaining the internal acidity thereof. This maintenance is essential for a variety of physiological functions such as: sorting of membrane and organellar proteins; proinsulin conversion; neurotransmitter uptake; cellular degradative processes; and, receptor cycling. See Mellman et al., Ann. Rev. Biochem., 55, 663-699 (1986); Forgac, Physiological Rev., 69, 765-796 (1989); Stevens and Forgac, Annu. Rev. Cell. Dev. Biol., 13, 779-808 (1997); Nelson, TIPS, 12, 71-75 (1991).

Vacuolar-type (H+)-ATPase activity is also located within specialized plasma membranes. Important examples include the vacuolar-type (H+)-ATPase activity in the plasma membranes of kidney intercalated cells, osteoclasts and sperm cells. See Stone and Xie, Kidney Int., 33, 767-774 (1988); Vaananen et al., J. Cell, Biol., 111, 1305-1311 (1990); Blair et al., Science, 245, 855-857 (1987); Wang and Gluck, J. Biol. Chem., 265, 21957-21965 (1990); Hall and Chambers, Inflamm. Res., 45, 1-9 (1996); Hall and Schaueblin, Bone and Mineral, 27, 159-166 (1994); David and Baron, Exp. Opin. Invest. Drugs, 4, 725-740 (1995); Wassarman, Science, 235, 553-560 (1987); Nelson, TIPS, 12, 71-75 (1991).

Because of the importance of vacuolar-type (H+)-ATPase activity in the maintenance of many physiological functions, compounds which inhibit vacuolar-type (H+)-ATPase will have useful pharmacological applications in a variety of different situations. See reviews by Nelson, TIPS, 12, 71-74 (1991), and Keeling et al., Ann. New York Acad. Sci., 834, 600-608 (1997), and references contained therein. For example, a given vacuolar-type (H+)-ATPase inhibitor may have utility against one or more disease states or physiological functions, in which it is desirable to inhibit an intra-organellar, vacuolar-type (H+)-ATPase-mediated process, such as acidification, accumulation of a neurotransmitter, receptor turnover, lysosomal storage, and the like. See Mellman et al., Ann. Rev. Biochem., 55, 663-699 (1986); Forgac, Physiological Rev., 69, 765-796 (1989); Stevens and Forgac, Annu. Rev. Cell. Dev. Biol., 13, 779-808 (1997); Nelson, TIPS, 12, 71-75 (1991). Similarly, a given vacuolar-type (H+)-ATPase inhibitor may be useful against one or more disease states or physiological functions, in which it is desirable to modify a plasma membrane vacuolar-type (H+)-ATPase-mediated process, such as urinary acidification, bone resorption, or the acrosomal acid secretion required for fertility. See Stone and Xie, Kidney Int., 33, 767-774 (1988); Vaananen et al, J. Cell. Biol., 111, 1305-1311 (1990); Blair et al., Science, 245, 855-857 (1987); Wang and Gluck, J. Biol. Chem., 265, 21957-21965 (1990); Hall and Chambers, Inflamm. Res., 45, 1-9 (1996); Hall and Schaueblin, Bone and Mineral, 27, 159-166 (1994); David and Baron, Exp. Opin. Invest. Drugs, 4, 725-740 (1995); Wassarman, Science, 235, 553-560 (1987); Nelson, TIPS, 12, 71-75, (1991). Compounds that inhibit vacuolar-type (H+)-ATPases also will have important utility for cancer therapy. For example, there is literature evidence indicating involvement of vacuolar-type (H+)-ATPases in processes related to cellular proliferation, angiogenesis, tumor cell invasiveness, metastasis, and drug resistance (see, e.g., Akifusa et. al., Exp. Cell Res., 238, 82-89 (1998); Altan et al., J. Exp. Med., 187, 1583-1598 (1998); Gerard et al., J. Exp. Biol., 201, 21-31 (1998); Ishii et al., J. Antibiot., 48, 12-20 (1995); Moriyama et al., J. Biochem., 115, 213-218 (1994); Ohkuma et al., In Vitro Cell Devel. Biol., 29A, 862-866 (1993); Perona et al., Nature, 334, 438-440 (1988); Montcourrier et al., J. Cell Sci., 107, 2381-2391 (1994); Montcourrier et al., Clin. Exp. Metastatis, 15, 382-392 (1997); Martinez-Zaguilan et al., Ann. NY Acad. Sci., 671, 478-480 (1992); Martinez-Zaguilan et al., Am. J. Physiol., 265, C1015-C1029 (1993); Martinez-Zaguilan et al., J. Cell. Physiol., 176, 196-205 (1998); Nishihara et al., Biochem. Biophys. Res. Commun., 212, 255-262 (1995); Manabe et al., J. Cell Physiol., 157, 445-452 (1993); Kinoshita et al., FEBS Lett., 337, 221-225 (1994); Kinoshita et al., FEBS Lett., 398, 61-66 (1996); Ohta et al., Brit. J. Cancer, 73, 1511-1517 (1996); Ohta et al., J. Pathol., 185, 324-330 (1998); Marquardt et al., J. Natl. Cancer Inst., 83, 1098-1102 (1991); and Banderra et al., Int. J. Oncol., 12, 711-715 (1998)). Therefore, compounds that inhibit these phenomena will be useful in cancer chemotherapy.

Among the numerous challenges faced by medicinal chemistry research is the challenge of identifying new vacuolar-type (H+)-ATPase-inhibitory leads applicable to medical treatments. In addition, the identification and development of new leads useful in cancer chemotherapy remains a perplexing problem. Purely synthetic approaches toward the identification of novel anticancer agents and vacuolar-type (H+)-ATPase inhibiting agents have been typically unsuccessful, partly due to the technological and human limitations inherent in laboratory synthesis. Although biological metabolites provide a vast resource of new structurally diverse chemical compounds, the number of agents available for exploiting therapeutic opportunities are relatively few, particularly inhibitors of vacuolar-type (H+)-ATPase. For example, structural types that potently and selectively inhibit vacuolar-type (H+)-ATPases have thus far been limited to compounds such as bafilomycins, concanamycins, and benzolactone enamides, such as the salicylihalamides and lobatamides (see Boyd, PCT International Patent Application No. PCT/US00/05582).

Thus, there remains a need for new vacuolar-type (H+)-ATPase inhibitors and anticancer compounds, pharmaceutical compositions, and methods of using them. The present invention provides such compounds, compositions comprising such compounds, and methods of use. These and other advantages of the present invention, as well as additional inventive features, will be apparent from the description of the invention provided herein.

BRIEF SUMMARY OF THE INVENTION

The present invention provides a compound of the formula:

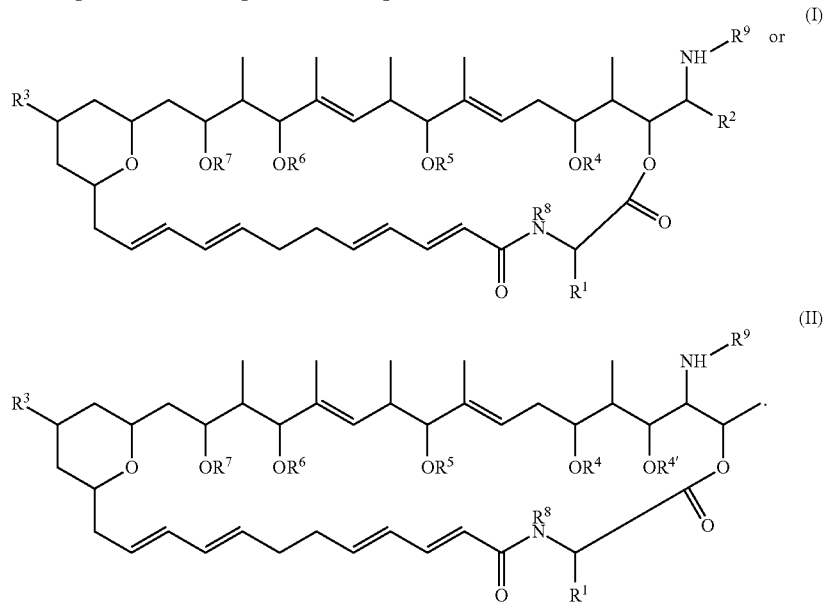

Substituent $R^1$ is H, a straight-chain or branched saturated alkyl, a straight-chain or branched unsaturated alkyl, or an aryl, wherein $R^1$ is unsubstituted or substituted with one or more substituents, which are the same or different, selected from the group consisting of oxo (=O), $OR^{1a}$, $CO_2R^{1a}$, and $OC(O)R^{1a}$, wherein $R^{1a}$ is H, a straight-chain or branched saturated alkyl, a straight-chain or branched unsaturated alkyl, or an aryl.

Substituent $R^2$ is H, a straight-chain or branched saturated alkyl, a straight-chain or branched unsaturated alkyl, or an aryl, wherein $R^2$ is unsubstituted or substituted with one or more substituents, which are the same or different, selected from the group consisting of oxo (=O), $OR^{2a}$ or $OC(O)R^{2a}$, wherein $R^{2a}$ is H, a straight-chain or branched saturated alkyl, a straight-chain or branched unsaturated alkyl, or an aryl.

Substituent $R^3$ is H, a straight-chain or branched saturated alkyl, a straight-chain or branched unsaturated alkyl, or an aryl.

Substituents $R^{4'}$ and $R^4$-$R^8$ are the same or different and each is $R^{10}$, $C(O)R^{10}$ or $SO_2R^{10}$, wherein $R^{10}$ is H, a straight-chain or branched saturated alkyl, a straight-chain or branched unsaturated alkyl, or an aryl, wherein $R^{10}$ is unsubstituted or substituted with one or more substituents, which are the same or different, selected from the group consisting of oxo (=O), $OR^{10a}$, $CO_2R^{10a}$ and $OC(O)R^{10a}$, wherein $R^{10a}$ is H, a straight-chain or branched saturated alkyl, a straight-chain or branched unsaturated alkyl, or an aryl.

Substituent $R^9$ is $R^{9a}$, $C(O)R^{9a}$ or $SO_2R^{9a}$, wherein $R^{9a}$ is H, a straight-chain or branched saturated alkyl, a straight-chain or branched unsaturated alkyl, or an aryl, wherein $R^{9a}$ is unsubstituted or substituted with one or more substituents, which are the same or different, selected from the group consisting of oxo (=O), $OR^{9b}$, $OC(O)R^{9b}$, $OSO_2R^{9b}$, $NHR^{9b}$, $NHC(O)R^{9b}$ and $NHSO_2R^{9b}$, wherein $R^{9b}$ is H, a straight-chain or branched saturated alkyl, a straight-chain or branched unsaturated alkyl, or an aryl, wherein $R^{9b}$ is unsubstituted or substituted with one or more substituents, which are the same or different, selected from the group consisting of oxo (=O), $OR^{9c}$, $CO_2R^{9c}$ and $OC(O)R^{9c}$, wherein $R^{9c}$ is H, a straight-chain or branched saturated alkyl, a Straight-chain or branched unsaturated alkyl, or an aryl.

Substituents $R^{1a}$, $R^{2a}$, $R^{10a}$ and $R^{9c}$ can be unsubstituted or substituted with one or more substituents selected from the group consisting of halogen, amino, hydroxyl, oxo (=O), thio, cyano and nitro. The compound of the present invention can be in the form of a pharmaceutically acceptable salt or a prodrug.

The present invention additionally provides a composition comprising a therapeutically effective amount of at least one compound of the present invention, alone or in combination with at least one additional therapeutic agent. The therapeutically effect amount can be a vacuolar-type (H+)-ATPase-inhibiting effective amount and/or an anticancer effective amount.

The present invention further provides a method of prophylactically or therapeutically treating a condition treatable by the inhibition of vacuolar-type (H+)-ATPase, and a method of prophylactically or therapeutically treating cancer.

The compound(s) used in accordance with the present invention can be administered alone or in combination with a therapeutically effective amount of at least one additional therapeutic agent other than a compound of the present invention. Additional therapeutic agents include, for example, vacuolar-type (H+)-ATPase inhibitors and anticancer compounds.

DETAILED DESCRIPTION OF THE INVENTION

Figure 1A:
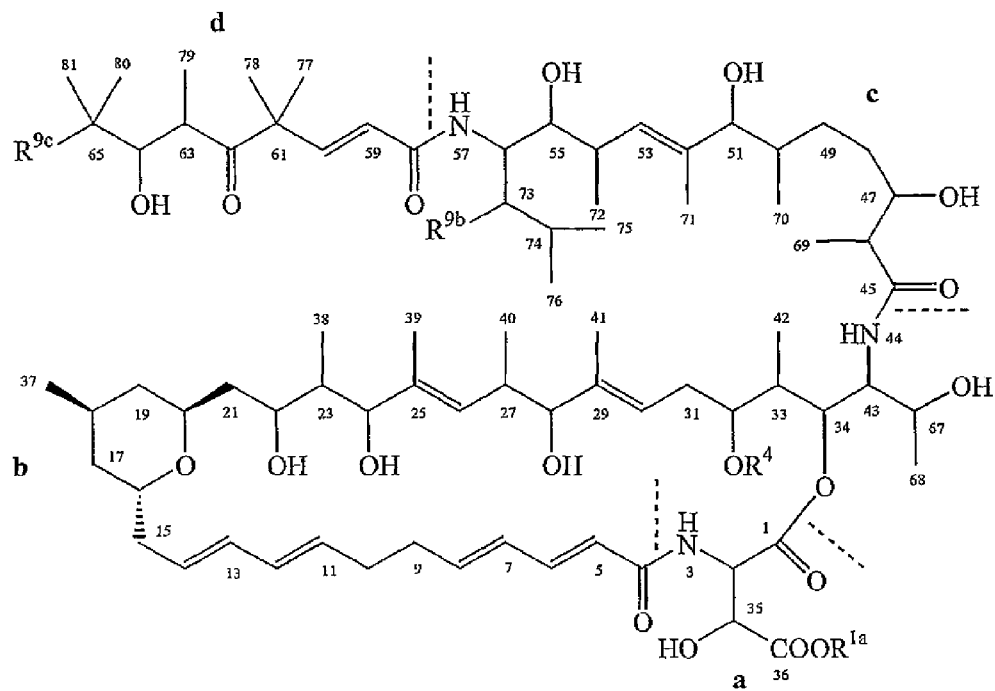
FIG. 1A illustrates the structures of chondropsin A (1), chondropsin B (2), a methylated derivative of chondropsin A (3), a deoxy derivative of chondropsin A (4); a methylated derivative of deoxy chondropsin A (5); chondropsin C (6); and a methylated derivative of chondropsin C (7).
Figure 1A:
Figure 1A:
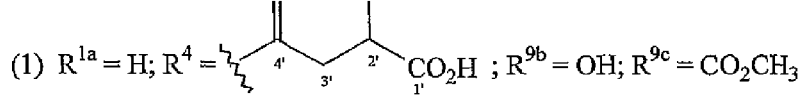
Figure 1A:
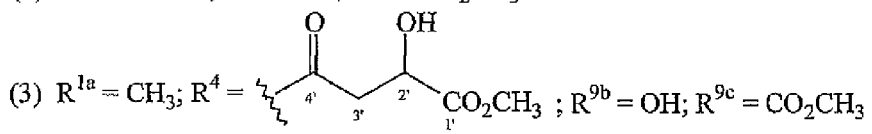
Figure 1B:
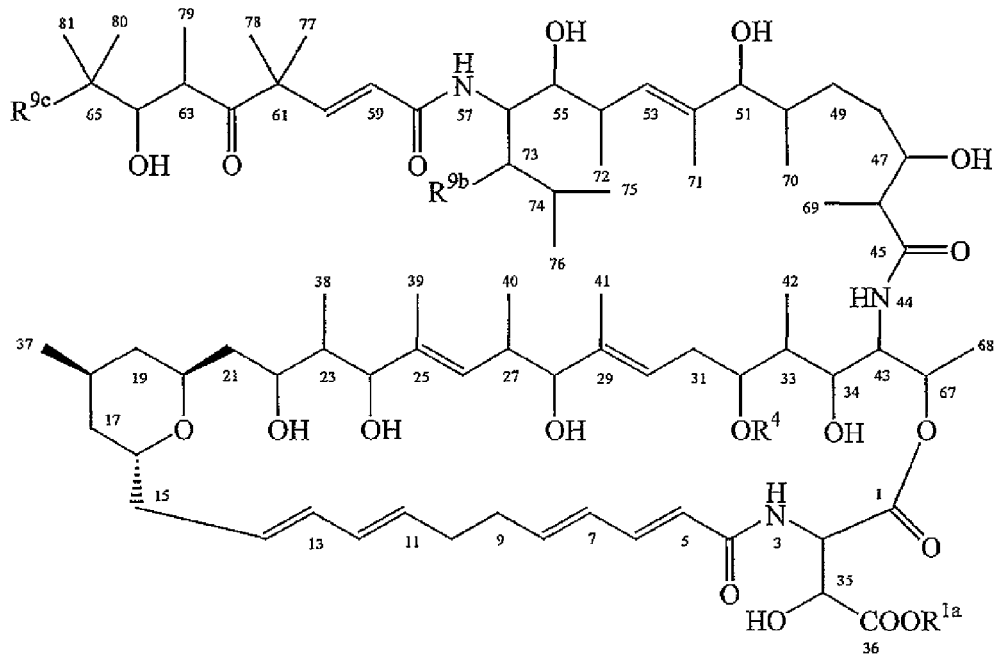
FIG. 1B illustrates the structure of chondropsin D (8) and a methylated analog thereof (9).
Figure 1B:
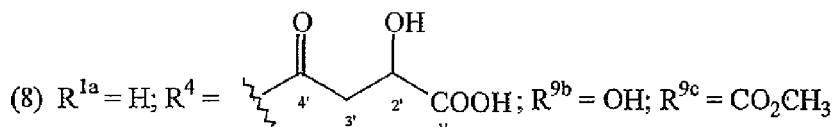
Figure 1B:
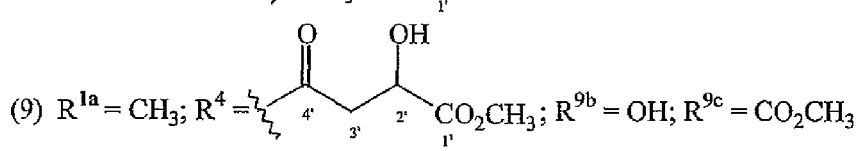

The present invention provides a compound of the formula:

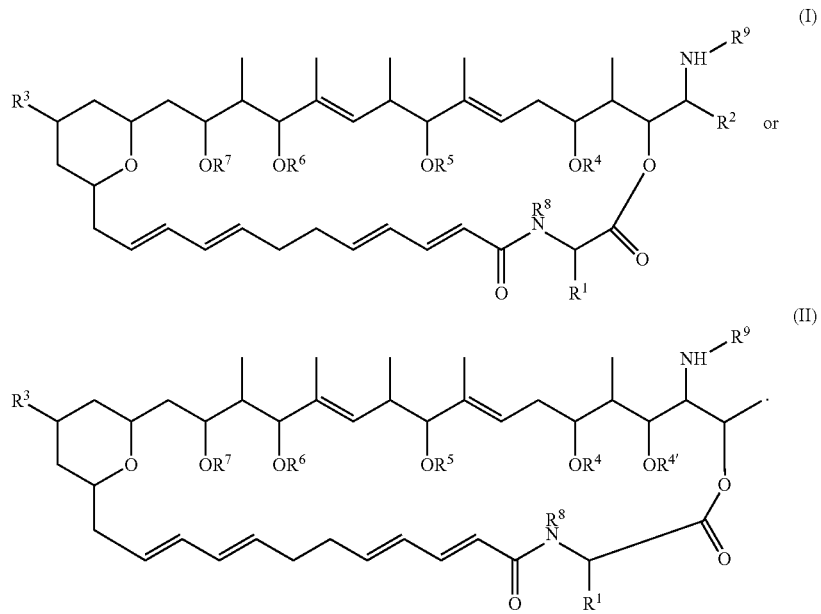

Substituent $R^1$ is H, a straight-chain or branched saturated alkyl, a straight-chain or branched unsaturated alkyl, or an aryl, wherein $R^1$ is unsubstituted or substituted with one or more substituents, which are the same or different, selected from the group consisting of oxo (=O), $OR^{1a}$, $CO_2R^{1a}$, and $OC(O)R^{1a}$, wherein $R^{1a}$ is H, a straight-chain or branched saturated alkyl, a straight-chain or branched unsaturated alkyl, or an aryl.

Substituent $R^2$ is H, a straight-chain or branched saturated alkyl, a straight-chain or branched unsaturated alkyl, or an aryl, wherein $R^2$ is unsubstituted or substituted with one or more substituents, which are the same or different, selected from the group consisting of oxo (=O), $OR^{2a}$ or $OC(O)R^{2a}$, wherein $R^{2a}$ is H, a straight-chain or branched saturated alkyl, a straight-chain or branched unsaturated alkyl, or an aryl.

Substituent $R^3$ is H, a straight-chain or branched saturated alkyl, a straight-chain or branched unsaturated alkyl, or an aryl.

Substituents $R^{4'}$ and $R^4$-$R^8$ are the same or different and each is $R^{10}$, $C(O)R^{10}$ or $SO_2R^{10}$, wherein $R^{10}$ is H, a straight-chain or branched saturated alkyl, a straight-chain or branched unsaturated alkyl, or an aryl, wherein $R^{10}$ is unsubstituted or substituted with one or more substituents, which are the same or different, selected from the group consisting of oxo (=O), $OR^{10a}$, $CO_2R^{10a}$ and $OC(O)R^{10a}$, wherein $R^{10a}$ is H, a straight-chain or branched saturated alkyl, a straight-chain or branched unsaturated alkyl, or an aryl; and Substituent $R^9$ is $R^{9a}$, $C(O)R^{9a}$ or $SO_2R^{9a}$, wherein $R^{9a}$ is H, a straight-chain or branched saturated alkyl, a straight-chain or branched unsaturated alkyl, or an aryl, wherein $R^{9a}$ is unsubstituted or substituted with one or more substituents, which are the same or different, selected from the group consisting of oxo (=O), $OR^{9b}$, $OC(O)R^{9b}$, $OSO_2R^{9b}$, $NHR^{9b}$, $NHC(O)R^{9b}$ and $NHSO_2R^{9b}$, wherein $R^{9b}$ is H, a straight-chain or branched saturated alkyl, a straight-chain or branched unsaturated alkyl, or an aryl, wherein $R^{9b}$ is unsubstituted or substituted with one or more substituents, which are the same or different, selected from the group consisting of oxo (=O), $OR^{9c}$, $CO_2R^{9c}$ and $OC(O)R^{9c}$, wherein $R^{9c}$ is H, a straight-chain or branched saturated alkyl, a straight-chain or branched unsaturated alkyl, or an aryl.

Substituents $R^{1a}$, $R^{2a}$, $R^{10a}$ and $R^{9c}$ can be unsubstituted or substituted with one or more substituents selected from the group consisting of halogen, amino, hydroxyl, oxo (=O), thio, cyano and nitro. The compounds of the present invention also can be in the form of a pharmaceutically acceptable salt. Pharmaceutically acceptable salts include, for example, the salt of one or more acidic substituents (e.g., a carboxylic acid salt, a sulfonic acid salt, and the like) and the salt of one or more basic substituents (e.g., the salt of an amine and the like). Suitable salts of acidic substituents include, for example, metal salts (e.g., sodium salts, potassium salts, magnesium salts, zinc salts, and the like) and ammonium salts (e.g., $NH_4^+$ salts, alkyl ammonium salts, quaternary ammonium salts, and the like). Suitable salts of basic substituents include, for example, acid addition salts (e.g., hydrochloride salts, hydrobromide salts, carboxylate salts (e.g., acetate salts)), sulfate salts, sulfonate salts (e.g., mesylate salts), phosphate salts, quaternary ammonium salts, and the like.

It will be appreciated that the compounds of the present invention can be in the form of a prodrug. Such prodrugs can be prepared using reagents and synthetic transformations that are well-known to those having ordinary skill in the art. The effectiveness of a particular prodrug can be determined using one or more analytical methods (e.g., pharmacokinetics, bioassays, in vivo efficacy studies, and the like) that are well-known to those of ordinary skill in the art.

Preferred substituents for $R^1$ include substituents of the formula $CHOR^{1a}CO_2R^{1a}$, wherein $R^{1a}$ is as defined herein. When $R^1$ is $CHOR^{1a}CO_2R^{1a}$, $R^{1a}$ is preferably H or an alkyl such as, for example, methyl, in which case $R^1$ includes substituents such as $CHOHCO_2H$, $CHOHCO_2CH_3$, $CH(OCH_3)CO_2H$ and $CH(OCH_3)CO_2CH_3$.

Preferred substituents for $R^2$ include substituents of the formula $CHOR^{2a}CH_3$, wherein $R^{2a}$ is as defined herein. When $R^2$ is $CHOR^{2a}CH_3$, $R^{2a}$ is preferably H, such that $R^2$ is $CHOHCH_3$.

Substituent $R^3$ preferably is an alkyl substituent, which is most preferably methyl.

Preferred substituents for $R^{4'}$ and $R^4$ include substituents of the formula $C(O)CH_2CHOHCO_2R^{10}$, wherein $R^{10}$ is as defined herein. When $R^{4'}$ or $R^4$ is of the formula C(O)

$CH_2CHOHCO_2R^{10}$, $R^{10}$ is preferably H or an alkyl substituent such as, for example, methyl.

In a preferred embodiment, $R^1$ is $CHOR^{1a}CO_2R^{1a}$, $R^2$ is $CHOR^{2a}CH_3$ and $R^4$ is $C(O)CH_2CHOHCO_2R^{10}$, wherein $R^1$, $R^{1a}$, $R^2$, $R^{2a}$, $R^4$ and $R^{10}$ are as defined herein.

While $R^5$-$R^8$ can be any combination of suitable substituents as defined herein, it is preferred that $R^5$-$R^8$ are H or $C(O)R^{10}$, wherein $R^{10}$ is as defined herein. In a preferred embodiment, all of $R^5$-$R^8$ are H.

Preferred $R^9$ substituents include $C(O)R^{9a}$ substituents of the formula:

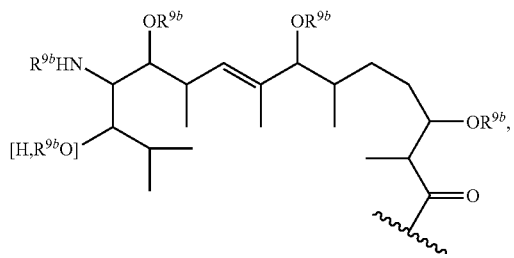

(A)

wherein $R^{9b}$ is as defined herein. While $R^{9b}$ can be any suitable substituent, $R^{9b}$ is preferably H or a substituent of the formula:

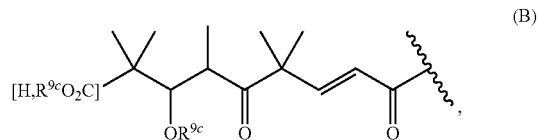

(B)

wherein $R^{9c}$ is as defined herein. When $R^{9b}$ is of formula (B), $R^{9c}$ is preferably H or methyl. Most preferably, the terminal substituent of formula (B) is $R^{9c}O_2C$, wherein $R^{9c}$ is H or methyl.

In a preferred embodiment, $R^9$ is $C(O)R^{9a}$, wherein $R^{9a}$ is an unsaturated alkyl substituted with one or more $OR^{9b}$ and $NHC(O)R^{9b}$ substituents. The $R^{9b}$ substituent of $NHC(O)R^{9b}$ is preferably an unsaturated alkyl substituted with one or more substituents selected from the group consisting of oxo, $OR^{9c}$, and $CO_2R^{9c}$. In a particularly preferred embodiment, $R^9$ is of the formula:

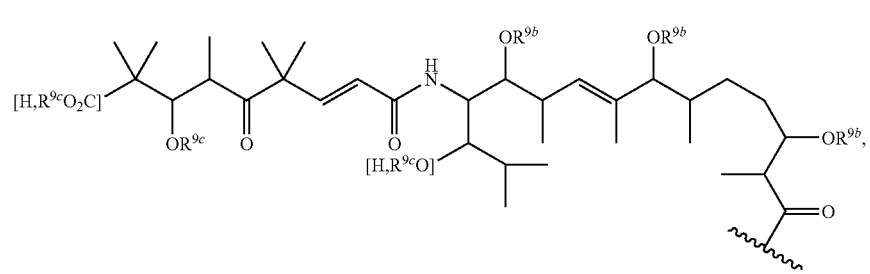

(C)

which corresponds structurally to the macrocyclic amino substituents in chondropsins A-D. When $R^9$ is of formula (C), one or more of the $R^{9b}$ substituents preferably is H (e.g., all of the $OR^{9b}$ substituents are hydroxyls), the $R^{9b}$ substituent of the terminal $R^{9c}O_2C$ ester preferably is hydrogen or methyl, and the other $R^{9c}$ substituent preferably is hydrogen.

Exemplary compounds of the present invention include compounds of the formulae:

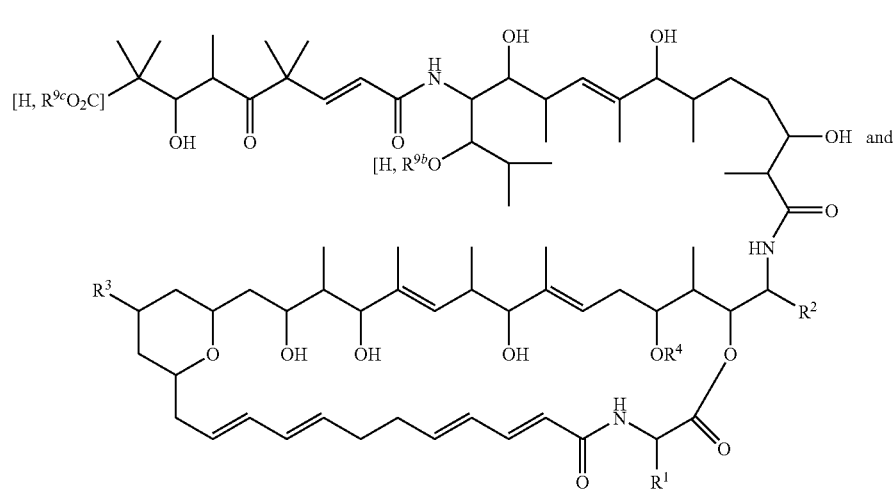

(D)

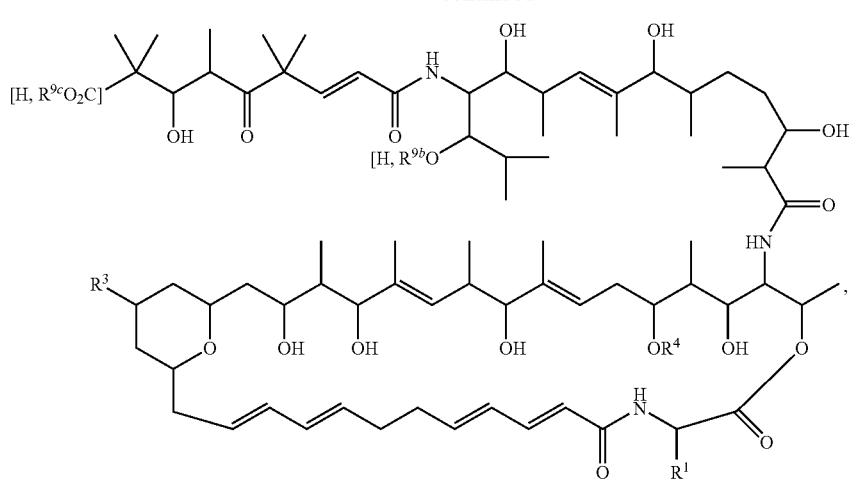

(E)

wherein $R^1$-$R^4$, $R^{9b}$ and $R^{9c}$ are as defined herein. When the compound of the present invention is of formula (D) or (E), it is preferred that $R^1$ is $CHOR^{1a}CO_2R^{1a}$, $R^2$ is $CHOR^{2a}CH_3$ and $R^3$ is methyl, wherein $R^{1a}$ is H or methyl and $R^{2a}$ is H. More preferably, $R^1$ is $CHOR^{1a}CO_2R^{1a}$, $R^2$ is $CHOR^{2a}CH_3$, $R^3$ is methyl, $R^4$ is H or $C(O)CH_2CHOHCO_2R^{10}$, wherein the $R^{1a}$ substituent on the alcohol oxygen is H, the $R^{1a}$ on the carboxylate oxygen is H or methyl, $R^{2a}$ is H, and $R^{10}$ is H or methyl. When the compound of the present invention is of formula (D) or (E), it is further preferred that $R^{9b}$ is hydrogen, and $R^{9c}$ is hydrogen or methyl.

The term "saturated alkyl" means a straight-chain or branched-chain saturated alkyl which can contain from 1 to about 30 carbon atoms, for example, from 1 to about 20 carbon atoms, from 1 to about 10 carbon atoms, from 1 to about 8 carbon atoms, or from 1 to about 6 carbon atoms. Examples of saturated alkyls include methyl, ethyl, propyl, isopropyl, n-butyl, sec-butyl, isobutyl, tert-butyl, pentyl, isoamyl, hexyl, octyl, dodecanyl, octadecanyl, and the like. Saturated alkyl substituents can be unsubstituted or substituted, for example, with at least one substituent selected from the group consisting of a halogen, a nitro, an amino, a hydroxyl, a thio, an acyl, an alkyl, and a cyano.

The term "unsaturated alkyl" means saturated alkyl (straight-chain or branched-chain), as defined herein, in which one or more of the single carbon-carbon bonds thereof is instead a multiple bond, for example, a double or a triple bond. Thus, unsaturated alkyls include alkenyl and alkynyl substituents, as well as substituents that have a combination of double and triple bonds.

The term "alkenyl" means a straight-chain or branched-chain alkenyl having one or more double bonds. Unless otherwise specified, the alkenyl can contain from 2 to about 30 carbon atoms, for example, from 2 to about 20 carbon atoms, from 2 to about 10 carbon atoms, from 2 to about 8 carbon atoms, or from 2 to about 6 carbon atoms. Examples of alkenyls include vinyl, allyl, 1,4-butadienyl, isopropenyl, substituents of formulae (A)-(C) as described herein, and the like.

The term "alkynyl" means a straight-chain or branched-chain alkynyl radical having one or more triple bonds. Unless otherwise specified, alkynyls can contain from 2 to about 30 carbon atoms, for example, from 2 to about 20 carbon atoms, from 2 to about 10 carbon atoms, from 2 to about 8 carbon atoms, or from 2 to about 6 carbon atoms. Examples of alkynyls include ethynyl, propynyl (propargyl), butynyl, and the like. Unsaturated alkyl substituents can be unsubstituted or substituted, for example, with at least one substituent selected from the group consisting of a halogen, a nitro, an amino, a hydroxyl, a thio, an acyl, an alkyl, and a cyano.

The term "aryl" means an aromatic carbocyclic radical, as commonly understood in the art, and includes monocyclic and polycyclic aromatics such as, for example, phenyl and naphthyl rings. Preferably, the aryl comprises one or more six-membered rings including, for example, phenyl, naphthyl, biphenyl and the like. Typically, the aryl comprises six or more carbon atoms in the ring skeleton thereof (e.g., from 6 to about 10 carbon atoms in the ring skeleton). Aryl substituents can be unsubstituted or substituted, for example, with at least one substituent selected from the group consisting of a halogen, a nitro, an amino, a hydroxyl, a thio, an acyl, an alkyl, and a cyano.

It will be appreciated that the compounds of the present invention can be obtained by methods known to those of ordinary skill in the art, for example, by structurally modifying chondropsin A or B, or by direct synthesis, using routine synthetic transformations that are well-known in the art. One or more hydroxyl groups, for example, can be converted to the oxo derivative by direct oxidation. Direct oxidation can be accomplished using any known method such as, for example, a Swern oxidation, or by reaction with a metal oxidant, such as a chromium oxide (e.g., chromium trioxide), a manganese oxide (e.g., manganese dioxide or permanganate) or the like. Primary alcohols can be oxidized to aldehydes, for example, via Swern oxidation, or they can be oxidized to carboxylic acids (e.g., $CO_2H$), for example, by reaction with a metal oxidant as described herein. Similarly, thiols (e.g., SR, SH or the like) can be converted to oxidized sulfur derivatives (e.g., $SO_2R$, $SO_3H$, or the like) by reaction with an appropriate oxidant.

One or more hydroxyl groups can be converted to an ester (e.g., $CO_2R$), for example, by reaction with an appropriate esterifying agent such as, for example, an anhydride (e.g., $(R(CO))_2O$) or an acid chloride (e.g., R(CO)Cl), or the like. One or more hydroxyl groups can be converted to a sulfonate (e.g., $SO_2R$) by reaction with an appropriate sulfonating agent such as, for example, a sulfonyl chloride (e.g., $RSO_2Cl$), or the like, wherein R is any suitable substituent including, for example, organic substituents described herein. Ester derivatives also can be obtained, for example, by reacting one or more carboxylic acid substituents (e.g., $CO_2H$) with an alkylating agent such as, for example, a diazoalkane (e.g., diazomethane), an alkyl or aryl iodide, or the like. One or more amides can be obtained by reaction of one or more carboxylic acids with an amine under appropriate amide-forming conditions. Appropriate amide-forming conditions include, for example, activation of a carboxylic acid (e.g., by conversion to an acid chloride or by reaction with a carbodiimide reagent) followed by coupling of the activated species with a suitable amine.

One or more hydroxyl groups also can be converted to a halogen atom using a halogenating agent such as, for example, an N-halosuccinimide such as N-iodosuccinimide, N-bromosuccinimide, N-chlorosuccinimide or the like, in the presence of a suitable activating agent (e.g., a phosphine or the like). One or more hydroxyl groups also can be converted to an ether by reacting one or more hydroxyls, for example, with an alkylating agent in the presence of a suitable base. Suitable alkylating agents can include, for example, an alkyl or aryl sulfonate, an alkyl or aryl halide, or the like. One or more suitably activated hydroxyls, for example, a sulfonate ester, and/or one or more suitably active halides, can be converted to the corresponding thiol, cyano, halo, or amino derivative by displacement with a nucleophile. Suitable nucleophiles can include, for example, a thiol, a cyano, a halide ion, an amine (e.g., $NH_2R^9$, wherein $R^9$ is as described herein), or the like.

Functional groups such as, for example, amines can be obtained by a variety of methods known in the art. Amines can be obtained by hydrolysis of one or more amides such as, for example, one or more of the amides in chondropsin A or B. Amines also can be obtained by reacting one or more suitable oxo groups (e.g., an aldehyde or a ketone) with one or more suitable amines under the appropriate conditions, for example, reductive amination conditions, or the like. One or more amines, in turn, can be converted to a number of other useful derivatives such as, for example, amides, sulfonamides and the like.

Other structural modifications can be accomplished by incorporating synthetic, semisynthetic or naturally occurring materials such as, for example, one or more amino acids, into the structure of one or more compounds of formula (I) or (II). For example, modifications of $R^1$ and/or $R^8$ can be accomplished by incorporating different amino acids into the macrocyclic ring skeleton of formula (I) or (II). Such amino acids can include, for example, aspartic acid, phenyl alanine, serine, leucine, analogs thereof, homologs thereof, and the like. It will be appreciated that a number of other synthetic transformations can be accomplished, other than those described herein, using routine chemistry that is well-known in the art. For example, compounds of formula (II) can be obtained synthetically by treating a compound of formula (I) under conditions suitable to promote ring expansion reaction (e.g., a based-promoted rearrangement of a compound of formula (I)), and the like. Specific transformations and structural modifications described herein are in no way limiting, but are only illustrative for preparing various compounds of the present invention.

Surprisingly and unexpectedly, it has been found that compounds of formulae (I) and (II) have anticancer activity and, even more surprisingly, vacuolar-type (H+)-ATPase inhibitory activity. The compounds of the present invention can be obtained by one of ordinary skill in the art by isolation from natural sources; chemical synthesis using well-known and readily available chemical reactions, reagents, and procedures; by semisynthesis; or the like. The structures of formulae (I) and (II) further provide a practical template that can be used to produce a vast number of structurally diverse, yet synthetically accessible, vacuolar-type (H+)-ATPase inhibitors and anticancer compounds.

One or more compounds of the present invention can be included in a composition, e.g., a pharmaceutical composition. In that respect, the present invention further provides a composition that includes at least one compound of the present invention and a pharmaceutically acceptable carrier. The composition of the present invention preferably includes a therapeutically effective amount of at least one compound of the present invention. The therapeutically effective amount can include an amount that is produces a therapeutic or prophylactic response in a patient to whom a compound or composition of the present invention is administered. A therapeutically effective amount can include, for example, a vacuolar-type (H+)-ATPase-inhibiting effective amount and/or an anticancer effective amount.

The composition of the present invention can further include a therapeutically effective amount of at least one additional compound other than a compound of the present invention, for example, a compound other than a compound of formula (I) or (II). When an additional compound is included in the composition of the present invention, the additional compound can be a vacuolar-type (H+)-ATPase-inhibiting compound (e.g., a concanamycin or a bafilomycin or a benzolactone enamide, such as a salicylihalamide or a lobatamide). One or more additional anticancer compounds, other than a compound of the present invention, also can be included. When the additional compound is a vacuolar-type (H+)-ATPase-inhibitor other than a compound of the present invention, it is preferably present in the composition in a vacuolar-type (H+)-ATPase-inhibiting effective amount. When the additional compound is an anticancer compound, it is preferably present in the composition of the present invention in an anticancer effective amount.

The composition of the present invention can be produced by combining one or more compounds of the present invention with an appropriate pharmaceutically acceptable carrier, and can be formulated into a suitable preparation. Suitable preparations include, for example, preparations in solid, semi-solid, liquid, or gaseous forms such as tablets, capsules, powders, granules, ointments, solutions, suppositories, injections, inhalants, and aerosols, and other formulations known in the art for their respective routes of administration. In pharmaceutical dosage forms, a compound of the present invention can be used alone or in appropriate association, as well as in combination, with other pharmaceutically active compounds, including other vacuolar-type (H+)-ATPase inhibiting compounds, as described herein.

Any suitable carrier can be utilized. Suitable carriers include pharmaceutically or physiologically acceptable carriers. The following methods and carriers are merely exemplary and are in no way limiting. In the case of oral preparations, a compound of the present invention can be administered alone or in combination with a therapeutically effective amount of at least one other compound. The active ingredient(s) can be combined, if desired, with appropriate additives to make tablets, powders, granules, capsules, or the like.

Suitable additives can include, for example, lactose, mannitol, corn starch or potato starch. Suitable additives also can include binders, for example, crystalline cellulose, cellulose derivatives, acacia, corn starch, or gelatins; disintegrants, for example, corn starch, potato starch or sodium carboxymethylcellulose; with lubricants such as talc or magnesium stearate. If desired, other additives such as, for example, diluents, buffering agents, moistening agents, preservatives, and/or flavoring agents, and the like, can be included in the composition.

The compounds used in accordance with the present invention can be formulated into a preparation for injection by dissolution, suspension, or emulsification in an aqueous or nonaqueous solvent, such as vegetable oil, synthetic aliphatic acid glycerides, esters of higher aliphatic acids, or propylene glycol (if desired, with conventional additives such as solubilizers, isotonic agents, suspending agents, emulsifying agents, stabilizers, and preservatives). The compounds of the present invention also can be made into an aerosol formulation to be administered via inhalation. Such aerosol formulations can be placed into pressurized acceptable propellants such as dichlorodifluoromethane, propane, nitrogen, and the like. The compounds of the present invention can be formulated into suppositories by admixture with a variety of bases such as emulsifying bases or water-soluble bases. The suppository formulations can be administered rectally, and can include vehicles such as cocoa butter, carbowaxes, and polyethylene glycols, which melt at body temperature, but are solid at room temperature.

Unit dosage forms for oral or rectal administration such as syrups, elixirs, and suspensions can be provided wherein each dosage unit, e.g., teaspoonful, tablespoonful, tablet, or suppository contains a predetermined amount of the composition containing the compound of the present invention. Similarly, unit dosage forms for injection or intravenous administration can comprise a composition as a solution in sterile water, normal saline, or other pharmaceutically acceptably carrier.

The term "unit dosage form" as used herein refers to physically discrete units suitable as unitary dosages for human and animal subjects, each unit containing a predetermined quantity of at least one compound or compounds of the present invention (alone or, if desired, in combination with another therapeutic agent). The unit dosage can be determined by methods known to those of skill in the art, for example, by calculating the amount of active ingredient sufficient to produce the desired effect in association with a pharmaceutically acceptable carrier. The specifications for the unit dosage forms that can be used in accordance with the present invention depend on the particular effect to be achieved and the particular pharmacodynamics associated with the compound(s) in the individual host.

Pharmaceutically acceptable carriers, for example, vehicles, adjuvants, excipients, or diluents, are accessible to those of skill in the art and are typically available commercially. One skilled in the art can easily determine the appropriate method of administration for the exact formulation of the composition being used. Any necessary adjustments in dose can be readily made by a skilled practitioner to address the nature or severity of the condition being treated. Adjustments in dose also can be made on the basis of other factors such as, for example, the individual patient's overall physical health, sex, age, prior medical history, and the like.

The compounds of the present invention can be utilized in a variety of therapeutic and non-therapeutic applications. It will be appreciated that one or more compounds of the present invention can be used, for example, as a control in diagnostic kits, bioassays, or the like. Preferably, the method of the present invention is applied therapeutically, for example, toward the treatment or prevention of cancer or toward the treatment or prevention a condition (e.g., an abnormal condition or a disease) treatable by the inhibition of vacuolar-type (H+)-ATPase. The compound(s) of the present invention can be administered alone, or in combination with a therapeutically effective amount of at least one additional compound other than a compound of the present invention.

Accordingly, the present invention further provides a method of therapeutically or prophylactically treating a condition treatable by the inhibition of vacuolar-type (H+)-ATPase, which method includes administering to a patient a vacuolar-type (H+)-ATPase-inhibiting amount of at least one compound of the present invention. More particularly, the present invention provides a method of therapeutically or prophylactically treating a condition treatable by the inhibition of vacuolar-type (H+)-ATPase, which method includes administering a vacuolar-type (H+)-ATPase inhibiting-effective amount of at least one compound of formula (I) or (II).

A number of conditions can be treated in accordance with the method of the present invention. The vacuolar-type (H+)-ATPase inhibiting compounds and compositions of the present invention can be used medically to regulate biological phenomena including, but not limited to: intra-organellar acidification of intracellular organelles; urinary acidification; bone resorption; fertility; angiogenesis; cellular invasiveness (e.g., tumor cell invasiveness); tumor cell proliferation and metastasis; and the development of drug resistance in tumor cells. The compounds of the present invention are therefore useful in the treatment of diseases that can be controlled by the inhibition of vacuolar-type (H+)-ATPase. Such diseases include, for example, osteoporosis (see, e.g., Keeling et al., *Ann. New York Acad. Sci.,* 834, 600-608 (1997)), Alzheimer's disease, glaucoma, and abnormal urinary acidification (see, e.g., Nelson, *TIPS,* 12, 71-75 (1991)). Moreover, the vacuolar-type (H+)-ATPase inhibitors of the present invention can be used in the treatment or prevention of diseases which utilize an acid-promoted cell penetration mechanism. For example, the compounds of the present invention can be used to inhibit the entry of viruses (e.g., baculoviruses and retroviruses), or to inhibit the entry of protein toxins (e.g., diphtheria toxin), into cells (see, e.g., Mellman et al., *Ann. Rev. Biochem.,* 55, 663-699 (1986)). The compoundS of the present invention also can be used to inhibit fertility in an animal, for example, a human (see, e.g., Wassannan, *Science,* 235, 553-560 (1987)), or to inhibit the proliferation, invasiveness or metastasis of tumor cells, or to promote the sensitivity of cancer toward drugs by inhibiting the ability of cancer cells to develop resistance to drugs, thereby facilitating and/or making possible the chemotherapeutic treatment of cancer (see, e.g., Marquardt and Center, *J. Natl. Cancer Inst.,* 83, 1098-1102 (1991)).

Thus, as indicated above, the methods of the present invention include a method of prophylactically or therapeutically treating conditions selected from the group consisting of osteoporosis, Alzheimer's disease, glaucoma, fertility, abnormal urinary acidification, abnormal secretion of degradative enzymes, and cancer. In accordance with method of the present invention, it is preferred that a vacuolar-type (H+)-ATPase inhibiting-effective amount is used. In that regard, it is preferred that the vacuolar-type (H+)-ATPase inhibiting-effective amount is effective to inhibit one or more conditions selected from the group consisting of intra-organellar acidification of intracellular organelles, urinary acidification, bone resorption, fertility, drug-resistance of tumor cells, tumor cell proliferation, cellular invasiveness, angiogenesis, and metastasis.

The method of the present invention further includes administering a vacuolar-type (H+)-ATPase inhibiting-effective amount of at least one additional compound other than a compound of the present invention, e.g., a compound other than a compound of formula (I) or (II). In some instances, the method of the present invention can be made more effective by administering one or more other vacuolar-type (H+)-ATPase inhibitors (e.g., a concanamycin and/or a bafilomycin and/or benzolactone enamide, such as a salicylihalamide or a lobatamide), along with a compound of the present invention. One or more compounds of the present invention also can be co-administered in combination with an anticancer agent other than a compound of the present invention, for example, to inhibit the development of cancer cell resistance to the anticancer agent.

In accordance with the method of the present invention, one or more compounds of the present invention can be administered by any suitable route including, for example, oral administration, intramuscular administration, subcutaneous, intravenous administration, or the like. For example, one or more vacuolar-type (H+)-ATPase inhibitors of the present invention (or a composition thereof) can be administered as a solution that is suitable for intravenous injection or infusion, a tablet, a capsule, or the like, or in any other suitable composition or formulation as described herein.

The vacuolar-type (H+)-ATPase "inhibiting-effective amount," as utilized in accordance with the composition and method of the present invention, includes the dose necessary to achieve a vacuolar-type (H+)-ATPase "inhibiting-effective level" of the active compound in an individual patient. The vacuolar-type (H+)-ATPase inhibiting-effective amount can be defined, for example, as that amount required to be administered to an individual patient to achieve a vacuolar-type (H+)-ATPase inhibiting-effective blood level, tissue level, and/or intracellular level of a compound of the present invention to effect the desired medical treatment.

When the effective level is used as the preferred endpoint for dosing, the actual dose and schedule can vary depending, for example, upon interindividual differences in pharmacokinetics, drug distribution, metabolism, and the like. The effective level also can vary when one or more compounds of the present invention are used in combination with other therapeutic agents, for example, one or more additional vacuolar-type (H+)-ATPase inhibitors, anticancer compounds, or a combination thereof. Moreover, the effective level can vary depending upon the disease for which treatment is desired. For example, the effective level for the treatment of osteoporosis may vary relative to the effective level required for the treatment of abnormal urinary acidification, or for the inhibition of fertility.

The unique vacuolar-type (H+)-ATPase inhibitory activity of the compounds of the present invention can be determined using any suitable method known in the art, for example, assay methods. A suitable assay method for measuring vacuolar-type (H+)-ATPase inhibitory activity is described, for example, in Chan et al., *Anal. Biochem.*, 157, 375-380 (1986). Alternatively, the unique vacuolar-type (H+)-ATPase inhibitory activity of the compounds of the present invention can be demonstrated using the NCI's 60 cell-line, human tumor, disease-oriented screen, which can accurately predict the anticancer activity of chemical compounds. Significantly, the NCI 60 cell-line screen also is a powerful tool that can be used to predict other types of biological activity, not limited to anticancer activity. In particular, the NCI 60 cell-line screen can be used to accurately predict antitumor activity as well as vacuolar-type (H+)-ATPase inhibitory activity (see Boyd, PCT International Patent Application No. PCT/US00/05582).

Irrespective of vacuolar-type (H+)-ATPase inhibitory activity, the compounds of the present invention have anticancer activity against a number of different cancer cell lines, including human cancers, as demonstrated in the NCI 60 cell-line screen. Exemplary compounds of the present invention possess potent antitumor activity (see, e.g., Example 3). To the extent that the compounds used in accordance with the present invention have anticancer activity, the effective blood level can be determined by analogy, based on the effective blood level corresponding to anticancer activity. As indicated above, the NCI 60 cell-line human tumor screen measures the ability of a compound to kill or inhibit selectively the growth of diverse human cancers. Using this screen, it is shown that the compounds of the present invention are highly active against certain types of human solid tumors (e.g., non-small cell lung cancer, renal cancer, and melanoma) which are very resistant or completely resistant to existing anticancer drugs. It is also shown that the compounds of the present invention are active against many other types of human solid tumors and leukemia cancer cells. By these observations, and with other detailed analyses of tumor cellular response profiles, it can be demonstrated that the compounds of the present invention are novel anticancer agents having considerable promise, for example, as therapeutic agents for the treatment of human solid tumors.

The compounds of the present invention are thus new and broadly efficacious anticancer agents, which inhibit or destroy human leukemias, lymphomas, melanomas and solid tumors. Solid tumors may include lung cancer (e.g., non-small cell lung cancer), colon cancer, CNS cancer (e.g., brain cancer), melanoma, ovarian cancer, renal cancer, prostate cancer, head and neck cancer, testicular cancer, germ-line cancers, endocrine tumors, uterine cancer, breast cancer, sarcomas, gastric cancer, hepatic cancer, esophageal cancer, pancreatic cancer, and the like.

The need for new classes of anticancer drugs remains an urgent worldwide priority, which is being addressed effectively through new research and development applications of the NCI 60 cell-line screen. Reviews can be found, for example, in Boyd and Paull, *Drug Dev. Res.*, 34, 91-109 (1995); Weinstein et al., *Science*, 275, 343-349 (1997); and Grever and Chabner, In: *Cancer: Principles and Practice of Oncology*, 5th Ed. (DeVita, V. T., et al., eds.); Philadelphia: Lippincott-Raven, 1977, pp. 385-394. The NCI screen provides an unprecedentedly rich information content to support the identification of important new classes of anticancer drugs. For example, see Weinstein et al. (1997), supra; Greyer and Chabner, In: *Cancer: Principles and Practice of Oncology*, 5th Ed. (DeVita, V. T., et al., eds.), Philadelphia: Lippincott-Raven, 1977, pp. 385-394; and Sausville, In: *Anticancer Drug Development Guide: Preclinical Screening, Clinical Trials, and Approval* (Teicher, B. A., ed.), Totowa, N.J.: Humana Press, Inc., 1997, pp. 217-226.

Accordingly, the present invention further provides a method of therapeutically or prophylactically treating cancer, which method comprises administering an anticancer effective amount of at least one compound of the present invention. The anticancer effective amount can be determined by methods known in the art including, for example, by determining an amount to be administered effective to produce an "effective level" in the subject patient. The effective level can be chosen, for example, as that level (e.g., $10^{-11}$-$10^{-7}$M from Example 3 herein) effective to inhibit the proliferation of tumor cells in a screening assay. Similarly, the effective level can be determined, for example, on the basis of the blood or tissue level in a patient that corresponds to a concentration of a therapeutic agent that effectively inhibits the growth of human cancers in an assay that is clinically predictive of anticancer activity. Further, the effective level can be determined, for example, based on a concentration at which certain markers of cancer in a patient's blood are inhibited by a particular compound that inhibits cancer. Alternatively, the effective level can be determined, for example, based on a concentration effective to slow or stop the growth of a patient's cancer, cause a patient's cancer to regress or disappear, render a patient asymptomatic to a particular cancer, or improve a cancer patient's subjective sense of condition. The anticancer effective level can then be used to approximate (e.g., by extrapolation), or even to determine, the level which is required clinically to achieve a vacuolar-type (H+)-ATPase inhibiting-effective blood, tissue, and/or intracellular level to effect the desired medical treatment. It will be appreciated that the determination of the therapeutically effective amount clinically required to effectively inhibit vacuolar-type (H+)-ATPase activity requires consideration of other variables that can influence the effective level, as discussed herein. When a fixed effective amount is used as a preferred endpoint for dosing, the actual dose and dosing schedule for drug administration can vary for each patient depending upon factors that include, for example, inter-individual differences in pharmacokinetics, drug disposition, metabolism, whether other drugs are used in combination, or other factors described herein that effect the effective level.

One skilled in the art can readily determine the appropriate dose, schedule, or method of administering a particular formulation, in order to achieve the desired effective level in an individual patient. One skilled in the art also can readily determine and use an appropriate indicator of the effective level of the compounds of the present invention. For example, the effective level can be determined by direct analysis (e.g., analytical chemistry) or by indirect analysis (e.g., with clinical chemistry indicators) of appropriate patient samples (e.g., blood and/or tissues). The effective level also can be determined, for example, by direct or indirect observations such as urine acidity, change in bone density, decrease in ocular pressure, or by the shrinkage or inhibition of growth of a tumor in a cancer patient (e.g., if the compound in question has anticancer activity). There are many references in the art that describe the protocols used in administering active compounds to a patient in need thereof. For example, the protocols used in the administration of anticancer agents to patients are described in "Cancer Chemotherapy: Principles and Practice" ed., Chabner and Collins, J. B. Lippincott, 1990, especially chapter 2, by J. B. Collins. See also Boyd, WO99/05136.

The present inventive method of prophylactically or therapeutically treating cancer further includes administering an anticancer effective amount of at least one additional compound other than a compound of the present invention, for example, a compound other than a compound of formula (I) or (II). For example, one or more compounds of the present invention can be co-administered with an anticancer agent, in which case the effective level desirably is the level needed to inhibit the ability of the cancer to develop resistance to the anticancer agent. Suitable anticancer compounds include, for example, all of the known anticancer compounds approved for marketing in the United States, and those that will become approved in the future, for which drug resistance thereto can be controlled by the inhibition of vacuolar-type (H+)-ATPase.

In accordance with the methods of the present invention, prophylaxis includes inhibition as described herein, e.g., inhibition of the growth or proliferation of cancer cells, or the inhibition of V-ATPase. The inhibition can be, but need not be, 100% inhibition in order to be prophylactically effective, and a clinically desirable benefit can be realized with less than 100% inhibition.

The demonstration of antitumor, vacuolar-type (H+)-ATPase-inhibitory and other biological activities can be based on the correlation of activity patterns generated in the NCI screen by compounds having known activity. The compounds compared in the correlation need not have particularly potent anticancer activity in order to display an activity pattern suitable for correlation in the NCI screen. Interestingly, compounds need not be structurally similar to one another in order correlate with each other in the NCI screen. Even if two structurally dissimilar compounds correlate strongly with each other in the NCI screen, they can be accurately predicted to have the same biological activity as each other in virtually any application, including non-cancer applications. For reviews pertinent to the NCI 60 cell-line screen, see Boyd, In: *Current Therapy in Oncology* (Niederhuber, ed.), Philadelphia: B.C. Decker, Inc., 1993, pp. 11-22; Boyd and Paull, *Drug Dev. Res.*, 34, 91-109 (1995); Greyer and Chabner, In: *Cancer Principles and Practice of Oncology*, 5th Ed. (DeVita et al., eds.), Philadelphia: Lippincott-Raven, 1977, pp. 385-394; Paull et al., In: *Cancer Chemotherapeutic Agents* (Foye, ed.), Washington, D.C.: American Chemical Society Books, 1995, pp. 9-45; and Weinstein et al., *Science*, 275, 343-349 (1997).

The NCI 60 cell-line human tumor screen measures the ability of a compound to kill or inhibit selectively the growth of diverse human cancers. Generally, in the NCI screen, the compounds of the present invention display potent activity against certain types of human solid tumors (e.g., non-small cell lung cancer, renal cancer, and melanoma), and resistant strains thereof. By these observations, and with other detailed analyses of the characteristic tumor cellular response profiles, it can be shown that the compounds of the present invention have a uniquely characteristic bioactivity profile.

The NCI 60 cell-line human tumor primary screen also provides a means by which to identify natural sources of compounds. The NCI screen was designed and implemented during 1985-1990 under the direction, close scrutiny, and supervision of several internationally comprised and renowned extramural (non-NCI) advisory and review groups, including the NCI Division of Cancer Treatment's Board of Scientific Counselors, an Ad Hoc Expert Review-Committee thereof, the National Cancer Advisory Board, and the President's Cancer Panel (see Boyd, In: *Anticancer Drug Development Guide: Preclinical Screening, Clinical Trials, and Approval* (Teicher, B. A., ed.), Totowa, N.J.: Humana Press, Inc., pp. 23-42, 1997). The impetus for development of the NCI screen was the international recognition that most of the commercially available anticancer drugs worldwide are essentially inactive or only transiently active against most forms of human cancer. Reviews are disclosed, for example, in Boyd, In: *Cancer: Principles and Practice of Oncology Updates* (DeVita, V. T., Jr., et al., eds), Philadelphia: Lippincott, 1989, pp. 11-22; and Boyd, In: *Current Therapy in Oncology* (Niederhuber, J. E., ed.), Philadelphia: BC Decker, 1993, pp. 11-22. Although this NCI screen has been operational only since 1990, it has already led to the discovery, development, and clinical use of significant new anticancer drugs in human cancer patients. For example, see Weinstein et al., *Science*, 275, 343-349 (1997); Greyer and Chabner, In: *Cancer: Principles and Practice of Oncology*, 5th Ed. (DeVita, V. T., et al., eds.), Philadelphia: Lippincott-Raven, 1977, pp. 385-394; and Sausville, In: *Anticancer Drug Development Guide: Preclinical Screening, Clinical Trials, and Approval* (Teicher, B. A., ed.), Totowa, N.J.: Humana Press, Inc., 1997, pp. 217-226.

The NCI screen consists of a panel of 60 different human tumor cell lines against which compounds are tested over a defined range of concentrations to determine the relative degree of growth inhibition or cytotoxicity against each cell line. The design and operation of the screen is such that for each compound tested, both the absolute and relative sensitivities of individual cell lines comprising the screen are sufficiently reproducible that a characteristic profile or "fingerprint" of cellular response is generated. Compounds that are active in the NCI screen show pronounced differential tumor growth-inhibitory and/or cytotoxic effects to the diverse cell lines comprising the 60 cell-line panel. The degree of differential response between the most and least sensitive lines typically may be relatively small (e.g., 2- to 10-fold), or occasionally as great as 3-4 orders of magnitude. Furthermore, the cell lines may be widely heterogeneous in response to a given compound, or they may be comparatively homogeneous, with only a relatively few lines showing much greater or lesser sensitivity than average. Regardless of the magnitude of the differential or the degree of heterogeneity of response of the cell line panel, it is the reproducibility of the response "fingerprint" that is important to the useful information contained therein.

Detailed disclosures of the screening assay are published, for example, in Monks et al., *J. Natl. Cancer Inst.*, 83, 757-766 (1991); Skehan et al., *J. Natl. Cancer Inst.*, 82, 1107-1112 (1990); and Boyd and Paull, *Drug Dev. Res.*, 34, 484-488 (1995). The identities, sources, derivation, morphology, and immunocytochemical characteristics, and methods of maintenance of the cell lines comprising the NCI 60 cell line panel have been described in detail, for example, in Boyd, In: *Cancer: Principles and Practice of Oncology Updates* (DeVita, V. T., Jr., et al., eds), Philadelphia: Lippincott, 1989, pp. 1-12; Monks et al., *J. Natl. Cancer Inst.* (1991), supra; Stinson et al., *Anticancer Res.*, 12, 1034-1035 (1992); and Boyd and Paull, *Drug. Dev. Res.*, 34, 91-109 (1995).

In the screening assay, each agent is tested over a broad concentration range against every cell line in the panel. All lines are inoculated onto a series of standard 96-well microtitre plates on day zero, followed by a 24 h incubation in the absence of the test compound. The inoculation densities employed depend upon the particular cell line and its growth characteristics. Inoculation densities used are as published in Monks et al., *J. Natl. Cancer Inst.* (1991), supra; and Boyd and Paull, *Drug Dev. Res.* (1995), supra. Test compounds are evaluated at five 10-fold dilutions. Following a 48-hour incubation with the test compound, the cells are assayed by the sulforhodamine B procedure as described in Skehan et al., *J. Natl. Cancer Inst.* (1990), supra; Monks et al., *J. Natl. Cancer Inst.* (1991), supra; and Rubinstein et al., *J. Natl. Cancer Inst.*, 82, 1113-1118 (1990). Optical densities are measured on automated plate readers, followed by computerized data acquisition, processing, storage, and availability for display and analysis.

Each successful test of a compound generates 60 dose-response curves, which are printed in the NCI screening data report as a series of composites comprising the tumor-type subpanels. Data for any individual cell line(s) failing quality control criteria, or otherwise deficient for any cell line(s) not tested successfully, are eliminated from further analysis and are deleted from the screening report.

The "percentage growth" (PG) term, and meaning of the +50, 0, and −50 response reference lines, the calculated response parameters, $GI_{50}$, TGI, and $LC_{50}$, construction and use of "mean-graphs" and the COMPARE pattern-recognition algorithms are briefly summarized as follows. The 50% growth inhibition parameter ($GI_{50}$) is the concentration of test drug where $100\times(T-T_o)/(C-T_o)=50=PG$. The optical density of the test well after the 48 hour drug exposure is T; the optical density at time zero is $T_o$; and the control optical density is C. The PG is a T/C-like parameter that can have values from +100 to −100. Whereas the $GI_{50}$ may be viewed as a growth-inhibitory level of effect, the TGI signifies a "total growth inhibition" or cytostatic level of effect. The TGI is the drug concentration where $100\times(T-T_o)/(C-T)=0=PG$. The $LC_{50}$ is the lethal concentration, "net cell killing" or cytotoxicity parameter. It is the concentration where $100\times(T-T_o)/T_o=-50=PG$. The control optical density is not used in the calculation of $LC_{50}$. For a detailed description of the "percentage growth" (PG) term, the +50, 0, and −50 response reference lines, the calculated response parameters, $GI_{50}$, TGI, and $LC_{50}$, the construction and use of "mean-graphs," and the COMPARE pattern-recognition algorithms, see Boyd et al., In: *Cytotoxic Anticancer Drugs: Models and Concepts for Drug Discovery and Development* (Valeriote, F A., et al., eds.), Amsterdam: Kluwer Academic Publishers, 1992, pp. 11-34; Monks et al., *J. Natl. Cancer Inst.* (1991), supra; and Boyd and Paull, *Drug Dev. Res.* (1995), supra.

A mean-graph is a pattern created by plotting positive and negative values, termed "deltas," generated from a set of $GI_{50}$, TGI, or $LC_{50}$ concentrations obtained for a given compound tested against each cell line in the NCI in vitro screen. The deltas are generated from the $GI_{50}$, TGI, or $LC_{50}$ data by a three-step calculation. For example, the $GI_{50}$ value for each cell line successfully tested against a given compound is converted to its $\log_{10} GI_{50}$ value. The mean panel $\log_{10} GI_{50}$ value is obtained by averaging the individual $\log_{10} GI_{50}$ values. Each $\log_{10} GI_{50}$ value then is subtracted from the panel mean to create the corresponding delta.

To construct the mean-graph, the deltas are plotted horizontally in reference to a vertical line that represents the calculated mean panel $GI_{50}$. The negative deltas are plotted to the right of the mean reference line, thereby proportionately representing cell lines more sensitive than the calculated average. Conversely, the positive deltas are plotted to the left of the reference line to represent the less sensitive cell lines to the given agent. Thus, for example, a bar projecting 3 units to the right of the vertical reference line in a $GI_{50}$ mean-graph indicates that the $GI_{50}$ concentration for that cell line is 1000 times less than the panel-averaged $GI_{50}$ concentration. The TGI and $LC_{50}$ mean-graphs are prepared and interpreted similarly.

Three additional numbers are printed at the base of each of the three respective mean-graphs. These numbers are the MG-MD, the Delta (not be confused with the "delta" for an individual cell line), and the Range. The MG-MD is the calculated mean panel $GI_{50}$, TGI, or $LC_{50}$. The Delta is the number of $\log_{10}$ units by which the delta of the most sensitive line(s) of the panel differ(s) from the corresponding MG-MD. Similarly, the Range is the number of $\log_{10}$ units by which the delta of the most sensitive line(s) of the panel differ(s) from the delta(s) of the least sensitive line(s).

COMPARE is a computerized, pattern-recognition algorithm used in the evaluation and exploitation of data generated by the NCI screen. In essence, COMPARE is a method of determining and expressing the degree of similarity, or lack thereof, of mean-graph profiles generated on the same or different compounds. An early impetus for the creation of such a tool during the development of the screen was the need to standardize and to establish and monitor the screen's consistency and reproducibility over time. This is accomplished by the regular testing of standard compounds that are expected to generate the same or very similar profiles when screened repetitively against the same panel of cell lines.

The NCI screen is repetitively calibrated. In the course of standardizing the screen, NCI selected as reference compounds approximately 170 agents for which a considerable amount of information was available about their preclinical and/or clinical anticancer properties and mechanism(s) of action. These compounds included commercially marketed anticancer drugs, investigational anticancer drugs, and other anticancer drugs which were or had been in preclinical development based upon activities in other cancer-related test systems. The repetitive periodic screening of these prototype "standard agents" (the cumulative compilation of results of which forms the "Standard Agents Database") remains the basis for calibration and standardization of the screen.

Significantly, the NCI's Standard Agent Database also provides a key to many useful new drug discovery applications. For example, the characteristic response profile "fingerprint" of a selected standard agent may be used as the "seed" to probe any other available mean-graph database to see if there are any closely matching profiles contained therein. Similarly, a profile selected from any available mean-graph database can be used to probe the "Standard Agent Database" to determine whether or not there are any closely matching standard agent profiles. Additional databases used for such studies may be constructed or defined as desired and may be relatively small (e.g., comprising a single compound or a selected congeneric series of compounds) or very large (e.g., the entire databases from all pure compounds, mixtures, fractions, and extracts tested in the NCI screen to date).

Initial NCI studies with COMPARE showed that compounds with matching mean-graph patterns often had related chemical structures. However, closer examination of this phenomenon revealed that certain compounds of unrelated structures had matching mean-graph patterns and shared the same or related biochemical mechanisms of action. For example, see Boyd, In: *Current Therapy in Oncology* (Niederhuber, J. E., ed.), Philadelphia: BC Decker, 1993, pp. 11-22; and Paull et al., In: *Cancer Therapeutic Agents,* Washington, D.C.: Am. Chem. Soc. Books, pp. 9-45 (1995); and references cited therein.

COMPARE analyses can be performed using the mean-graph deltas calculated from either the $GI_{50}$'s, the TGI's, or the $LC_{50}$'s. When a selected particular mean-graph profile or "seed" is used to probe a given database, the appropriate delta value for each cell line is compared to the corresponding delta value for the same cell line for every mean-graph entry in the specified database set. If either delta value is missing for any cell line (e.g., due to test failure or quality control deletion), then that cell line is eliminated entirely from the calculation for that particular seed/mean-graph and database/mean-graph pair. Thus, for each mean-graph in the specified database, a set of pairs (maximum of 60) of delta values is obtained. The commercially available SAS statistical program is used to calculate a Pearson product moment correlation coefficient (0.0-1.0) for each set of delta value pairs. The mean-graphs of all compounds in the specified database can then be rank-ordered for similarity to the seed mean-graph. Public access to the NCI's "Standard Agents Database," as well as to a variety of NCI screening data display and analysis tools, including COMPARE, are available to investigators worldwide via the Internet (http://dtp.nci.nih.gov/).

By regular application of COMPARE, using selected prototype seed compounds from the Standard Agents Database, NCI has maintained ongoing surveillance of the total historical screening database accrued from inception to date. In this manner, compounds with screening fingerprints matching standard agent(s) having known or presumed known mechanism(s) of actions can be identified. NCI has been able to associate and subsequently confirm the database classification of compounds of previously unknown mechanisms of action into a number of different known mechanistic classes of interest. For example, new members have been classified within general mechanistic categories of tubulin-interactive antimitotics, antimetabolites, alkylating agents, topoisomerase inhibitors, DNA binders, and the like. These and numerous other examples resulting from this kind of database prospecting have been published, for example, in Paull et al., *Cancer Res.,* 52, 3892-3900 (1992), and references cited therein; and Paull et al., In: *Cancer Chemotherapeutic Agents*, Washington, D.C.: Am. Chem. Soc. Books, 1995, pp. 9-45, and references cited therein.

Quite surprisingly, it has been discovered that, uniquely among the tens of thousands of mean-graph "fingerprints" analyzed, the characteristic screening "fingerprints" for certain exemplary compounds of the present invention correlate almost perfectly with those of protypical vacuolar-type (H+)-ATPase inhibitory compounds, concanamycin A, bafilomycin A1, salicylihalamide A and lobatamide A, all of which are structurally unrelated to the compounds of the present invention. The correlation for certain exemplary compounds of the present invention is so precise, that the possibility of coincidence is effectively ruled out. Indeed, the compounds of the present invention, whose mean graph fingerprints in the NCI screen correlate highly with those of concanamycin A, bafilomycin A1, salicylihalamide A, and lobatamide A, are inhibitors of vacuolar-type (H+)-ATPase. It has been confirmed by specific vacuolar-type (H+)-ATPase bioassay that compounds of the present invention whose fingerprints in the NCI 60 cell-line screen correlate with those of the structurally unrelated but known vacuolar-type (H+)-ATPase inhibitors (e.g., see Boyd, PCT International Patent Application No. PCT/US00/05582) concanamycin A, bafilomycin A1, salicylihalamide A and lobatamide A have potent vacuolar-type (H+)-ATPase inhibitory activity, as expected. Thus, the NCI 60 cell-line screen as well as specific vacuolar-type (H+)-ATPase bioassays can be used to demonstrate the vacuolar-type (H+)-ATPase inhibitory activity of one or more compounds of the present invention.

Compounds whose mean-graph "fingerprints" generated by the NCI 60 cell-line screen correlate highly with one another can be expected to share a common molecular target or biological mechanism of action, even if the compounds differ significantly in structure. A high correlation can be established, for example, by COMPARE correlation coefficients of approximately 0.8 to 0.9, or greater. See Boyd, In: *Current Therapy in Oncology* (Niederhuber, J. E., ed) Philadelphia: B.C. Decker, 1993, pp. 11-22; Boyd and Paull, *Drug Dev. Res.,* 34, 91-109, 1995; Paull et al., In: *Cancer Therapeutic Agents*, Washington, D.C.: Am. Chem. Soc. Books, 1995, pp. 9-45. Thus, the concanamycins, bafilomycins, salicylihalamides and lobatamides, and exemplary compounds of the present invention, for example, whose NCI 60 cell-line screen correlation coefficients with respect to each other are high, all can be shown to share the same molecular target, vacuolar-type (H+)-ATPase. Further illustration of this characteristic is provided in Example 4.

One skilled in the art will appreciate that vacuolar-type (H+)-ATPase inhibitors can inhibit the vacuolar-type (H+)-ATPase activity present in different kinds or locations of intracellular organelles, or in different kinds or locations of plasma membranes, or in different kinds or locations of cells or tissues. A given vacuolar-type (H+)-inhibitory compound may preferentially inhibit vacuolar-type (H+)-ATPase activity in one or more kind or location of intracellular organelle, plasma membrane, cell or tissue. Thus, the skilled practitioner will typically select a particular vacuolar-type (H+)-ATPase inhibitory compound for a desired therapeutic use. Compound selection can be based upon the particular kind or location of intracellular organelle or plasma membrane vacuolar-type (H+)-ATPase preferentially inhibited by the compound. Indeed, there are clear precedents in the literature to indicate that compounds can be selected for particular applications based upon preferential inhibition of one or more kind of vacuolar-type (H+)-ATPase over another. For example, Gagliardi et al., *J. Med. Chem.*, 41, 1568-1573, (1998), identified compounds that selectively inhibit human osteoclast vacuolar-type (H+)-ATPase activity compared to human renal cortical vacuolar-type (H+)-ATPase activity; such compounds, therefore, are expected to be particularly useful in treating osteoporosis.

In addition to inhibiting mammalian vacuolar-type (H+)-ATPase activity, the compounds of the present invention can be used to inhibit non-mammalian vacuolar-type (H+)-ATPase activity. For example, the known vacuolar-type (H+)-ATPase inhibitors bafilomycin $A_1$ and concanamycin A potently inhibit fungal as well as mammalian vacuolar-type (H+)-ATPase activity, and those compounds have strong antifungal activity. See Bowman et al., *Proc. Natl. Acad. Sci. USA*, 85, 7972-7976 (1988); Dröse et al., *Biochemistry*, 32, 3902-3906 (1993); Dröse and Altendorf, *J. Exp. Biol.*, 200, 1-8 (1997).

There is also evidence that vacuolar-type (H+)-ATPase plays important roles in the proliferation of tumor cells, and the consequent invasiveness and metastasis thereof. See Montcourrier et al., *J. Cell Sci.*, 107, 2381-2391 (1994); Martinez-Zaguilan et al., *Am. J. Physiol.*, 265, C1015-C1-29 (1993); Martinez-Zaguilan et al., *J. Cell Physiol.*, 176, 196-205 (1998); Nishihara et al., *Biochem. Biophys. Res. Commun.*, 212, 255-262 (1995); Manabe et al., *J. Cell Physiol.*, 157, 445-452 (1993). Furthermore, acidification of intracellular organelles can contribute to the sequestration and cellular efflux of conventional anticancer drugs. See Marquardt and Center, *J. Natl. Cancer Inst.*, 83, 1098-1102 (1991); Benderra et al., *Intl. J. Oncol.*, 12, 711-715 (1998); Mariyama et al., *J. Biochem.*, 115, 213-218 (1994). Therefore, vacuolar-type (H+)-ATPase inhibitory compounds of the present invention can be used to inhibit the proliferation of tumor cells, as well as the consequent invasiveness and metastasis thereof. Furthermore, the compounds of the present invention can be used to inhibit drug-resistance of tumor cells to conventional anticancer agents.

The particular compound or composition used in accordance with the present invention can be selected based upon the desired kind or site of vacuolar-type (H+)-ATPase inhibition, and/or based upon other pharmacological, toxicological, pharmaceutical or other pertinent considerations that are well-known to those skilled in the art. Routine methods for the specific bioassay, quantitation and comparisons of inhibitory activity of compounds and compositions of the present invention against vacuolar-type (H+)-ATPase activity in various tissues, cells, organelles and other preparations is well-documented in the literature (see, e.g., Bowman et al., *Proc. Natl. Acad. Sci. USA*, 85, 7972-7976 (1988); Gagliardi et al., *J. Med. Chem.*, 41, 1883-1893 (1998); Gagliardi et al., *J. Med. Chem.*, 41, 1568-1573 (1998); and references cited therein).

COMPARE analyses of $GI_{50}$ and TGI mean-graph screening profiles of certain compounds of the present invention can be consistently shown to have a high degree of commonality with respect to each other (e.g., $GI_{50}$ and TGI-COMPARE Pearson correlation coefficients of at least 0.6-0.8 or greater), but do not show any such correlations with any known standard agent. Similarly, extracts of natural organisms which can be shown to contain compounds of the present invention typically give $GI_{50}$ and TGI mean-graph screening fingerprints with similarly high $GI_{50}$ and TGI-COMPARE Pearson correlations (e.g., typically 0.6-0.7 or greater) to the compounds of the present invention. This allows a person of ordinary skill in the art to identify readily productive source organisms and extracts thereof, from which the compounds of the present invention or precursors thereof can be obtained. Identification and/or characterization of the present inventive compounds is further facilitated by the presence of certain characteristic NMR signals, such as described in Example 2. Such characteristic NMR signals can further confirm the identification and selection of compound mixtures, including crude extracts of natural organisms and partially purified fractions thereof, or synthetic or semi-synthetic reaction products, that contain the compounds.

Certain compounds of the present invention can be readily obtained from natural sources, including solvent extracts of marine sponges, for example, from aqueous extracts of sponge species from the genus *Chondropsis*. Extracts of *Chondropsis* sponges can be prepared from any suitable solvent, for example, organic solvents, water, and mixtures thereof. Fresh sponges can be used, but more generally they are frozen immediately after harvesting, and then are either used directly or are freeze-dried before the extraction is done. When a marine sponge is used as a source for obtaining compounds of the present invention, it is preferably from the genus *Chondropsis*, but is more preferably a *Chondropsis* species, and is most preferably a *Chondropsis* species collected near Bass Island, near Wollongong, Australia (see Example 1).

Specific extracts of *Chondropsis* species that contain compounds of the present invention can be identified and selected based upon the anticancer screening profile they produce in the NCI 60-cell human tumor screen. Such extracts containing compounds of the present invention also can be identified and selected based upon key proton and carbon NMR signals (e.g., see Tables 1, 2, and 5-8) that are characteristic of the structural component motif ((I) and (II)) shared by the compounds of the present invention (see also Example 1).

From the aforementioned selected extracts, a variety of methods can be used for isolation and purification of compounds of the present invention. During each step of isolation and purification, the aforementioned characteristic anticancer screening profile or a suitable bioassay, and the aforementioned characteristic proton NMR signals, can be obtained for intermediate fractions, as well as partially purified and purified compounds, to ensure isolation of the desired compounds of the present invention.

A preferred method of obtaining certain compounds of the present invention or a precursor thereof from natural source materials includes the steps of:

(a) obtaining a fresh or frozen sample of a marine sponge (or other suitable natural source material) that includes one or more compounds of the present invention or a precursor thereof, (b) extracting the sample with water and/or one or more organic solvents, or mixtures thereof, which dissolves the compound(s) or precursor(s) to form an extract, (c) optionally treating the extract with a solvent (e.g., a nonsolvent such as ethanol) to precipitate and remove high molecular weight proteins and sulfated polysaccharides, (d) optionally partitioning the extract between an organic solvent and an aqueous solvent to form a partitioned organic solvent extract or aqueous solvent extract containing the desired compound(s) or precursor(s), (e) chromatographing, one or more times as necessary, the partitioned extract, for example, on an adsorption, partition, or reversed-phase, or size-exclusion matrix, to produce one or more fractions, and (f) isolating one or more compounds of the present invention or one or more precursors thereof from one or more of the fractions.

In step (b), the solvent can include mixtures of suitable nonpolar organic solvents or suitable polar organic solvents. Suitable nonpolar organic solvents include, for example, $CH_2Cl_2$, $CHCl_3$, toluene, hexane and the like. Suitable polar organic solvents include, for example, water, MeOH, EtOH, isopropyl alcohol, acetone and the like.

In step (d) suitable organic nonpolar solvents include $CH_2Cl_2$, hexane, $CCl_4$, $CHCl_3$, MeOtBu, ethyl acetate and the like; and typical aqueous solvents can include, for example, mixtures of water and methanol. Non-limiting examples of solvent mixtures that can be used optionally in this partitioning step include: (1) $CH_2Cl_2$ and 19:1 $H_2O$-MeOH, (2) hexane and 9:1 MeOH—$H_2O$, (3) $CCl_4$ and 8:2 MeOH—$H_2O$, (4) $CH_2Cl_2$ and 7:3 MeOH—$H_2O$, and (5) EtOAc and $H_2O$.

In step (e), the chromatography preferably is column chromatography. When column chromatography is used, the chromatographic matrix preferably is the adsorption type, the partition type, the reversed-phase type, the size exclusion type, or a suitable combination thereof. Preferably, the solvent and/or the matrix is not acidic in nature when the compound to be isolated is not particularly acid-stable. Sephadex™ LH-20, a particularly preferred matrix for isolation of certain types of compounds of the present invention, combines three of the aforesaid matrix types, and is characterized by mild treatment and good recoveries. The isolation step (f) can be carried out, for example, by evaporating the solvent, by recrystallization optionally after additional concentration using reversed-phase HPLC, or by using other isolation procedures known in the art.

In a preferred isolation method, a selected sample of frozen *Chondropsis* species sponge is ground to a powder with dry ice. The dry ice is allowed to sublime, distilled $H_2O$ is added, and the thawed material is stirred for 3 h at 3° C., then centrifuged. The aqueous supernatant is lyophilized and the concentrated extract is fractionated on wide-pore reversed-phase $C_4$ media. The fraction eluting with MeOH—$H_2O$ (2:1) is further separated on an LH-20 column using a MeOH (7:3) solvent system. The early eluting material from this column is ultimately purified by reversed-phase $C_{18}$ HPLC with a linear MeOH—$H_2O$ gradient to give, after solvent removal, substantially purified compound(s) of the present invention. More specific illustrations of isolation of representative compounds of the present invention are given in Example 1.

The definitive proofs of structure of the isolated compounds can be obtained by a combination of methods including primary spectral analyses (e.g., high-resolution NMR and mass spectrometry, infrared and UV spectroscopy), comparisons of spectral and physico-chemical properties with related literature precedents, and by x-ray crystallographic analysis. Various structural proofs are illustrated in Example 2 herein.

EXAMPLES

The following examples further illustrate the present invention but, of course, should not be construed as in any way limiting its scope.

Example 1

This example demonstrates a procedure for obtaining exemplary compounds of the present invention from a marine sponge. This example further demonstrates the conversion of chondropsin A to a methylated analog, which also is a compound of the present invention.

The particular extract of a *Chondropsis* sp. sponge selected from the NCI Natural Products Repository, Frederick, Md., for investigation in the present example showed an NCI 60-cell screening mean-graph (TGI) fingerprint that was highly correlated (TGI-COMPARE Pearson correlation coefficient greater than or equal to about 0.6-0.7) to that of concanamycin A. The extract also showed proton and carbon NMR resonances at chemical shift values (and multiplicities) corresponding to pure samples of representative chondropsins (e.g., see Tables 1 and 2). The selected extract was from a *Chondropsis* sp. sponge that had been collected approximately 100 M from the shore of Bass Island off the coast of Wollongong, Australia. Samples were kept frozen prior to extraction. A voucher specimen of this particular sponge collection (coded as serial number Q66 C 1004) is on deposit at the Smithsonian Institution, Washington, D. C. Cantrell et al., *J. Am. Chem. Soc.*, 122, 8825-8829 (2000).

Chondropsins A (FIG. 1A, compound (1)) and B (FIG. 1A, compound (2)) were isolated as follows. The frozen sponge samples (357 g, wet weight) were ground in dry ice to a fine powder and extracted with $H_2O$ at 4° C. The aqueous extract was removed by centrifugation and subsequently lyophilized to give 44.0 g of extract. A 5 g aliquot of the aqueous extract was dissolved in 50 ml of distilled water and applied to a chromatography column (9 cm i.d.) containing 62 g of $C_4$ reversed-phase media (J. T. Baker, Wide-Pore™ Butyl). The column was eluted using increasing concentrations of methanol (MeOH) in $H_2O$. The fraction eluting with MeOH—$H_2O$ (2:1) was concentrated to provide 90 mg of material, which was further separated on a Sephadex LH-20 column (2.5×95 cm) eluted with MeOH—$H_2O$ (7:3). The early eluting fractions from the LH-20 column were concentrated to provide 29 mg of residue that were subsequently dissolved in 2 ml of MeOH—$H_2O$ (1:1) for HPLC. Reversed-phase HPLC separation (Dynamax ODS, 10×250 mm, 8 μm; flow rate, 4 ml/min) was performed using a linear MeOH—$H_2O$ gradient (from 65:35 to 85:15 over 40 min.) which provided 2 mg of (FIG. 1A, compound (1)) and 0.8 mg of (FIG. 1A, compound (2)). The remainder of the extract was processed in a similar manner to provide a total of 17 mg of (1) (0.005% wet weight) and 7 mg of (2) (0.002% wet weight).

Physicochemical and spectroanalytical data for chondropsin A (1) were as follows: colorless powder; $[\alpha]^{27}_D$ +7.1° (c 0.28, MeOH); UV[MeOH] $\lambda_{max}$ 229 (ε 15372), 259 (ε 16229) nm; IR $\upsilon_{max}$ (KBr) 3418, 3298, 1689, 1610, 1533, 1207 cm$^{-1}$; for $^1H$ and $^{13}C$ NMR, see Table 1; FABMS (negative ion; glycerol matrix) m/z 1587.0 [M-H]$^-$, HRFABMS (positive ion; magic bullet matrix; CsI-doped) m/z 1852.7305 [M-H+Cs$_2$]$^+$, calcd. for $C_{83}H_{132}N_3O_{22}Cs_2$, 1852.7208, Δ+9.7 mmu.

Physicochemical and spectroanalytical data for chondropsin B (2) were as follows: colorless powder; $[\alpha]^{27}_D$ +30.6° (c 0.36, MeOH); UV[MeOH] $\lambda_{max}$ 227 (ε 14792), 260 (ε 13124) nm; IR $\upsilon_{max}$ (KBr) 3422, 2957, 1695, 1635, 1207 cm$^{-1}$; for $^1H$ and $^{13}C$ NMR, see Table 2; FABMS (negative ion; glycerol matrix) m/z 1471.0 [M-H]$^-$, HRFABMS (positive ion; magic bullet matrix; CsI-doped) m/z 1604.8199 [M-H+Cs$_2$]$^+$, calcd. for $C_{79}H1_{129}N_3O_{22}Cs$, 1604.8122, Δ+7.7 mmu.

Methylation of chondropsin A (1) was performed as follows. A 5.5 mg solution of (1) in 2.8 ml of MeOH was treated at room temperature with a solution of $CH_2N_2$ in diethyl ether (3 ml). Removal of the solvent under a stream of $N_2$ and HPLC purification of the residue as described above for (1), provided 3.5 mg of the methylated derivative (FIG. 1A, compound (3)).

Physicochemical and spectroanalytical data for (3) were as follows: colorless powder; $[\alpha]^{27}{}_D$ +14.7° (c 0.34, MeOH); UV [MeOH] $\nu_{max}$ 228 ($\epsilon$ 20762), 261 ($\epsilon$ 20317) nm; IR $\nu_{max}$ (KBr) 3420, 3304, 1684, 1534, 1205, 1140 cm$^{-1}$; HRFABMS (positive ion; magic bullet matrix, CsI-doped) m/z 1748.8524 [M+Cs]$^+$, calcd. for $C_{85}H_{137}N_3O_{26}Cs$, 1748.8545, $\Delta$–2.0 mmu; $^1$H NMR (500 MHz, DMF-d$_7$) δ 11-2, 5.18 (1H, m); H-3, 8.13 (1H, br s); H-5, 6.31 (1H, d, J=15.0 Hz); H-6, 7.14 (1H, dd, J=11.0 and 15.0 Hz); H-7, 6.27 (1H, dd, J=11.0 and 15.0 Hz); H-8, 6.10 (1H, m); H-9, 2.30 (2H, m); H-10, 2.16 (2H, m); H-11, 5.69 (1H, m); H-12, 6.16 (1H, m); H-13, 6.16 (1H, m); H-14, 5.69 (1H, m); H-15, 2.09 (1H, m) and 2.74 (1H, m); H-16, 4.01 (1H, m); H-17, 1.29 (1H, m) and 1.47 (1H, m); H-18, 1.84 (1H, m); H-19, 0.80 (1H, m) and 1.52 (1H, m); H-20, 3.70 (1H, m); H-21, 1.23 (1H, m) and 1.48 (1H, m); H-22, 4.25 (1H, m); H-23, 1.43 (1H, m); H-24, 3.87 (1H, d, J=9.5 Hz); H-26, 5.14 (1H, d, J=2.2 Hz); H-27, 2.53 (1H, m); H-28, 3.57 (1H, m); H-30, 5.24 (1H, m); H-31, 2.08 (1H, m) and 2.43 (1H, m); H-32, 4.92 (1H, m); H-33, 2.08 (1H, m); H-34, 5.09 (1H, m); H-35, 4.80 (1H, br s); H-37, 0.87 (3H, d, J=6.6 Hz); H-38, 0.63 (3H, d, J=6.5 Hz); H-39, 1.60 (3H, s); H-40, 0.71 (3H, d, J=6.5 Hz); H-41, 1.56 (3H,s); H-42, 1.02 (3H, d, J=6.5); H-43, 4.16 (1H,m); H-44, 7.69 (1H, d, J=9.5 Hz); H-46, 2.54 (1H,m); H-47, 3.54 (1H, m);H-48, 1.48 (2H,m); H-49, 1.23 (1H,m) and 1.34 (1H,m); H-50, 1.55 (1H, m); H-51, 3.56 (1H, d, J=8.0 Hz); H-53, 5.50 (1H, d, J=10.0 Hz); H-54, 2.68 (1H,m); H-55, 3.79 (1H,m); H-56, 4.07 (1H,m); H-57, 7.67 (1H, d, J=9.5 Hz); H-59, 6.37 (1H, d, J=15.5 Hz); H-60, 6.87 (1H, d, J=15.5 Hz); H-63, 3.20 (1H, m); H-64, 4.05 (1H, d, J=8.5 Hz); H-67, 3.78 (1H, m); H-68, 1.08 (3H, d, J=6.0 Hz); H-69, 1.13 (3H, d, J=6.6 Hz); H-70, 0.95 (3H, d, J=7.0 Hz); H-71, 1.48 (3H,s); H-72, 1.00 (3H, d, J=7.0 Hz); H-73, 3.60 (1H,m); H-74, 1.47 (1H,m); H-75, 0.86 (3H, d, J=6.6 Hz); H-76, 0.93 (3H, d, J=7.0 Hz); H-77, 1.21 (3H,s); H-78, 1.27 (3H,s); H-79, 0.77 (3H, d, J=7.0 Hz); H-80, 1.11 (3H, s); H-81, 1.18 (3H,s); H-2', 4.53 (1H, m); H-3', 2.68 (1H,m) and 2.82 (1H, dd, J=4.0 and 16.0 Hz); C-36-OCH$_3$, 3.71 (3H,s); C-66-OCH$_3$, 3.63 (3H, s); C-1'-OCH$_3$, 3.67 (3H,s); $^{13}$C NMR (125 MHz, DMF-d$_7$), chemical shifts and assignments were deduced from HSQC and HMBC correlations, δ C-1, 171.4; C-2, 55.9; C-4, 167.4; C-5, 124.4; C-6, 140.7; C-7, 129.5; C-8, 141.7; C-9, 34.4; C-10, 32.8; C-11, 130.1; C-12, 131.8; C-13, 132.3; C-14, 132.1; C-15, 34.6; C-16, 72.6; C-17, 37.3; C-18, 25.9; C-19, 41.7; C-20, 66.0; C-21, 42.9; C-22, 66.0; C-23, 42.0; C-24, 80.1; C-25, 66.0; C-21, 42.9; C-22, 66.0; C-23, 42.0; C-24, 80.1; C-25, 137.7; C-26, 131.0; C-27, 36.4; C-28, 81.7; C-29, 138.8; C-30, 122.2; C-31, 31.9; C-32, 73.2; C-33, 37.9; C-34, 76.8; C-35, 72.3; C-36, 171.0; C-37, 22.8; C-38, 9.9; C-39, 11.2; C-40, 18.2; C-41, 11.1; C-42, 9.8; C-43, 53.6; C-45, 176.9; C-46, 47.2; C-47, 73.8; C-48, 33.2; C-49, 29.5; C-50, 36.3; C-51, 83.1; C-52, 137.1; C-53, 128.7; C-54, 34.9; C-55, 74.5; C-56, 53.7; C-58, 165.9; C-59, 124.7; C-60, 146.6; C-61, 51.3; C-62, 214.7; C-63, 44.7; C-64, 77.2; C-65, 46.7; C-66, 178.0; C-67, 68.8; C-68, 21.5; C-69, 15.6; C-70, 16.0; C-71, 11.9; C-72, 18.1; C-73, 75.7; C-74, 31.5; C-75, 19.6; C-76, 20.2; C-77, 23.8; C-78, 23.9; C-79, 15.4; C-80, 17.7; C-81, 25.3; C-1', 171.6; C-2', 68.6; C-3', 40.0; C-4', 172.7; C-36-OCH$_3$, 52.5; C-66-OCH$_3$, 51.7; C-1'-OCH$_3$, 51.8.

L-malic acid was methylated as follows. A solution of L-malic acid (135 mg) in 1 ml of MeOH was treated with less than one equivalent of CH$_2$N$_2$ at room temperature. After removal of the solvents, the crude reaction products (139 mg) were dissolved in 4 ml of MeOH and separated by HPLC using a cyano bonded-phase column (Dynamax CN, 10×250 mm, 8 μm; flow rate, 4 ml/min; UV detection at 210 nm) eluted with hexane-isopropyl alcohol (95:5). The C-1 and C-4 monomethyl ester derivatives of L-malic acid were obtained in approximately a 9:1 ratio in favor of the C-4 derivative, as expected.

Physicochemical and spectroanalytical data for malic acid C-4 monomethyl ester were as follows: GCMS (EI, positive ion) m/z 148.0370 [M]$^+$, calcd. for $C_5H_8O_5$, 148.0372, $\Delta$–0.1 mmu; $^1$H NMR (500 MHz, DMF-d$_7$) d 2.63 (1H, dd, J=7.5 and 15.5 Hz); 2.77 (1H, dd, J=5.0 and 15.5 Hz); 3.69 (3H, s); 4.52 (1H, dd, J=5.0 and 7.5 Hz); $^{13}$C NMR (125 MHz, DMF-d$_7$), d 174.2; 172.3; 68.4; 52.0; 39.8.

Physicochemical and spectroanalytical data for malic acid C-1 monomethyl ester were as follows: GCMS (EI, positive ion) m/z 148.0370 [M]$^+$, calcd. for $C_5H_8O_5$, 148.0372, $\Delta$–0.1 mmu; $^1$H NMR (500 MHz, DMF-d$_7$) d 2.65 (1H, dd, J=8.0 and 15.5 Hz); 2.83 (1H, dd, J=5.0 and 15.5 Hz); 3.65 (3H, s); 4.49 (1H, dd, J=5.0 and 8.0 Hz); $^{13}$C NMR (125 MHz, DMF-d$_7$), d 175.1; 171.6; 68.2; 51.7; 39.9.

General methods used in obtaining these data were as follows. Optical rotations were recorded on a Perkin-Elmer 241 polarimeter. UV spectra were recorded on a Beckman DU-640 spectrophotometer. FT-IR spectra were obtained on a Perkin-Elmer Spectrum 2000 spectrometer. High resolution mass spectra were measured on JOEL SX102 spectrometer. One- and two-dimensional $^1$H and $^{13}$C NMR spectra were recorded on a Varian INOVA-500 spectrometer equipped with Nalorac inverse detection and broadband probes. HPLC separations were performed on a Waters 600E system using a Waters 990 photodiode array detector.

Example 2

This example demonstrates the structural proofs of particular compounds of the present invention.

Chondropsin A (1), such as obtained and characterized spectroanalytically in Example 1, was a colorless powder with a molecular formula of $C_{83}H_{133}N_3O_{26}$ established as follows. Negative-ion FABMS analysis of (1) showed a strong pseudomolecular ion at m/z 1587.0, corresponding to [M-H]$^-$. Subsequent positive ion HRFABMS analysis of a CsI-doped sample of (1) detected an adduct containing two Cs atoms [M-H+Cs$_2$]$^+$, m/z 1852.7305 (calcd for $C_{83}H_{132}N_3O_{26}Cs_2$, 1852.7208, $\Delta$+9.7 mmu). The facile incorporation of two Cs ions suggested that (1) contained two carboxylic acid functionalities. Treatment of (1) with diazomethane provided the bis-methylated derivative (3) (HR-FABMS, CsI-doped, m/z 1748.8524 [M+Cs]$^+$), confirming the two carboxylic acid groups in (1). The molecular formula of (1), which was assigned as $C_{83}H_{133}N_3O_{26}$ based on the HRFABMS measurements, was consistent with a detailed analysis of the $^1$H and $^{13}$C NMR data (Table 1). Despite the relatively large number of protons and carbons in (1), the NMR spectra it provided were generally well-resolved and rich in structural information. However, ambiguities that did arise due to overlapping resonances required the analysis of complete NMR data sets in different solvents including DMF-d$_7$, DMSO-d$_6$, and CD$_3$OH. NMR spectral analyses revealed 19 methyl groups in (1), comprising one downfield methyl ester, three downfield vinyl methyls, 11 aliphatic methyl doublets, and four methyl singlets. Fifteen oxymethine groups, eight olefins, one ketone, and eight ester, amide or carboxylic acid carbonyls were also defined. Extensive 2-D NMR analysis of (1), particularly based on data from COSY, TOCSY, HSQC, and HMBC pulse sequences, resulted in the elucidation of five (a-e) structural fragments (FIG. 1A). The $^1$H and $^{13}$C NMR data for chondropsin A (1) in DMF-d$_7$ are shown in Table 1 below.

TABLE 1

| Position | $\delta_H$ Mult. (J, Hz) | $\delta_C$ Mult.[a] | HMBC[b] | HSQC-TOCSY[c] |
|---|---|---|---|---|
| 1 | — | 171.7 s | — | — |
| 2 | 5.14 dd (2.2, 9.2) | 55.6 d | 4, 35, 36 | 35 |
| 3 | 7.85 d (9.2) | — | 2, 4 | 2 |
| 4 | — | 167.4 s | — | — |
| 5 | 6.29 d (15.2) | 124.6 d[d] | 4, 7 | 6, 7, 8 |
| 6 | 7.14 dd (11.0, 15.2) | 140.5 d | 4, 8 | 5, 7, 8 |
| 7 | 6.29 dd (11.0, 15.0) | 129.9 d | — | 5, 6, 8, 9 |
| 8 | 6.10 m | 141.9 d | 6 | 5, 6, 7 |
| 9 | 2.30 m | 34.5 t[e] | 7, 8, 10 | 6, 7, 8, 10, 12 |
| 10 | 2.15 m | 32.9 t | 9 | 7, 8, 9, 12, 13 |
| 11 | 5.69 m | 131.2 d | 13 | 12, 13, 14 |
| 12 | 6.17 d (14.9) | 131.8 d | 10 | 10, 11, 13, 14, 15 |
| 13 | 6.17 d (14.9) | 132.2 d[f] | 12, 15 | 10, 11, 12, 14, 15, 16 |
| 14 | 5.69 m | 132.1 d | 13 | 11, 12, 13, 15, 16 |
| 15 | 2.03 m, 2.79 m | 34.6 t[e] | 16 | 12, 13, 14, 16 |
| 16 | 4.01 m | 72.3 d | — | 14, 15 |
| 17 | Hβ 1.27 m, Hα 1.48 m | 38.0 t | 15, 16 | — |
| 18 | 1.84 m | 26.0 d | — | 17, 19, 20, 37 |
| 19 | Hβ 0.80 m, Hα 1.52 m | 41.7 t | 17, 20 | 17, 18, 20, 21, 37 |
| 20 | 3.69 m | 65.9 d | — | 19, 21 |
| 21 | 1.46 m, 1.23 m | 43.0 t | 19, 20, 22 | 20, 22 |
| 22 | 4.25 m | 66.1 d | — | 20, 21 |
| 23 | 1.44 m | 41.9 d | 24, 38 | 22, 24 |
| 24 | 3.87 d (8.8) | 80.2 d | 22, 23, 25, 26, 38, 39 | 23, 38 |
| 25 | — | 138.2 s | — | — |
| 26 | 5.13 d (2.2) | 132.2 d[f] | 24, 27, 39, 40 | 27, 28 |
| 27 | 2.51 m | 36.5 d | 28, 40 | 26, 28, 40 |
| 28 | 3.53 d (8.1) | 82.4 d | 26, 29, 30, 41 | 27, 40 |
| 29 | — | 138.6 s | — | — |
| 30 | 5.25 dd (6.6, 6.6) | 123.6 d | 28, 31, 41 | 31, 32 |
| 31 | 2.05 m, 2.45 m | 32.1 t | 29, 30, 32 | 30, 32 |
| 32 | 4.90 m | 73.1 d | 42, 1' | 30, 31 |
| 33 | 2.03 m | 38.9 d | 35, 42 | 34 |
| 34 | 5.11 dd (3.3, 9.5) | 76.9 d | 1, 32, 33 | 33, 42 |
| 35 | 4.83 br s | 72.2 d | 1, 2, 36 | 2 |
| 36 | — | 171.8 s | — | — |
| 37 | 0.87 d (6.6) | 22.8 q | 17, 18, 19 | 17, 19 |
| 38 | 0.63 d (7.0) | 9.8 q | 22, 23, 24 | 23, 24 |
| 39 | 1.60 s | 11.2 q | 24, 25, 26 | 26 |
| 40 | 0.67 d (6.6) | 18.1 q | 26, 27, 28 | 26, 27, 28 |
| 41 | 1.56 s | 11.3 q | 28, 29, 30 | 30 |
| 42 | 1.03 d (7.0) | 9.7 q | 32, 33, 34 | 33, 34 |
| 43 | 4.15 m | 53.4 d | 45 | 67 |
| 44 | 7.55 d (9.9) | — | 45 | 43 |
| 45 | — | 176.8 s | — | — |
| 46 | 2.54 m | 47.2 d | 45, 47, 69 | 47, 69 |
| 47 | 3.53 m | 73.8 d | 45 | 46, 48, 49 |
| 48 | 1.48 m | 33.1 t | 47 | 47 |
| 49 | 1.21 m, 1.37 m | 29.6 t | 47 | — |
| 50 | 1.57 m | 36.2 d | — | 48, 49, 51 |
| 51 | 3.56 d (8.1) | 83.1 d | 49, 50, 52, 53, 70 | — |
| 52 | — | 137.2 s | — | — |
| 53 | 5.49 d (9.5) | 129.5 d | 51, 55, 71 | 54, 72 |
| 54 | 2.68 m | 35.4 d | — | 53, 72 |
| 55 | 3.76 m | 74.8 d | 53, 73 | 56 |
| 56 | 4.08 m | 53.6 d | 55, 58 | 55 |
| 57 | 7.58 d (10.3) | — | 58 | 55, 56 |
| 58 | — | 165.9 s | — | — |
| 59 | 6.36 d (15.4) | 124.7 d[d] | 58, 61 | 60 |
| 60 | 6.88 d (15.4) | 146.7 d | 58, 61, 62, 77, 78 | 59 |
| 61 | — | 51.3 s | — | — |
| 62 | — | 214.7 s | — | — |
| 63 | 3.20 dq (7.0, 10.0) | 44.7 d | 62, 64, 65, 79 | 64, 79 |
| 64 | 4.05 d (10.0) | 77.2 d | 63, 65, 80 | 63, 79 |
| 65 | — | 46.7 s | — | — |
| 66 | — | 178.0 s | — | — |
| 67 | 3.78 m | 69.2 d | — | 68 |
| 68 | 1.09 d (6.2) | 21.6 q | 43, 67 | 43, 67 |
| 69 | 1.14 d (6.6) | 15.7 q | 45, 47 | 46, 47 |
| 70 | 0.95 d (5.5) | 15.9 q | 49, 50, 51 | 49, 50, 51 |
| 71 | 1.48 s | 11.9 q | 51, 52, 53 | 53 |
| 72 | 1.01 d (6.9) | 18.1 q | 53, 54, 55 | 53, 54 |
| 73 | 3.61 m | 75.7 d | 55, 74, 76 | 74, 75, 76 |
| 74 | 1.48 m | 31.5 d | 73 | 73 |
| 75 | 0.87 d (6.6) | 19.6 q | 73, 74, 76 | 73, 74 |
| 76 | 0.94 d (6.2) | 20.1 q | 73, 75 | 73, 74 |

TABLE 1-continued

| Position | $\delta_H$ Mult. (J, Hz) | $\delta_C$ Mult.[a] | HMBC[b] | HSQC-TOCSY[c] |
|---|---|---|---|---|
| 77 | 1.21 s | 23.8 q[g] | 60, 61, 62, 78 | — |
| 78 | 1.27 s | 23.9 q[g] | 60, 61, 62, 77 | — |
| 79 | 0.76 d (6.6) | 15.4 q | 62, 63, 64 | 63, 64 |
| 80 | 1.11 s | 17.7 q | 64, 65, 66, 81 | — |
| 81 | 1.18 s | 25.3 q | 64, 65, 66, 80 | — |
| 1' | — | 172.6 s | — | — |
| 2' | 4.53 dd (4.0, 8.4) | 68.8 d | 1', 3', 4' | 3' |
| 3' | 2.60 dd (8.4, 15.8), 2.76 m | 40.2 t | 1', 2', 4' | 2' |
| 4' | — | 172.8 s | — | — |
| OCH$_3$ | 3.63 s | 51.7 q | 66 | |

[a]Multiplicity determined using the DEPT pulse sequence.
[b]Optimized for J = 3.5 and 8.5 Hz. Carbons correlated to the proton resonance(s) in the $^1$H column.
[c]Carbons correlated to the proton resonance(s) in the $^1$H column.
[d,e,f,g]Assignments may be interchanged.

Partial structure a was established as a linear, four-carbon fragment which consisted of a carboxylic acid, an ester carbonyl, a nitrogen-substituted methine (δ 55.6, C-2), and an oxymethine group (δ 72.2, C-35). The H-2 resonance (δ 5.14) showed COSY correlations both to H-35 (δ 4.83) and to a well-resolved amide proton at δ 7.85 (H-3). HMBC correlations from H-2 and H-3 to a carbonyl at δ 167.4 (C-4) confirmed the attachment of a to substructure b via an amide bond at N-3. At this point, it was not possible to distinguish which carbonyl in fragment a existed as a free carboxylic acid and which was part of an ester link. Three-bond heteronuclear correlations from either H-3, or the hydroxyl proton on C-35, might have facilitated assignment of these two carbonyls, however, no definitive HMBC correlations were observed, even when a variety of different NMR parameters and experimental conditions were explored. Similarly, no diagnostic NOE interactions were observed.

The structure of fragment b could be inferred largely from COSY and TOCSY correlation data. A proton spin system which contained two pairs of conjugated dienes separated by two allylic methylenes was apparent, and its proximity to partial structure a was defined by HMBC correlations from H-5 (δ 6.29) and H-6 (δ 7.14) to the C-4 amide carbonyl. It was also possible to establish in b the presence of a trisubstituted tetrahydropyran ring in which one oxymethine (δ 4.01, H-16) was coupled to the C-15 allylic methylene protons. The other oxygenated methine (δ 3.69, H-20) was coupled to the C-21 aliphatic methylene group, and a methyl group was substituted at C-18. Extension of the proton spin system through the highly overlapped C-17, C-19, and C-21 methylene protons to H-22 (δ 4.26) was aided by a combination of HMBC and HSQC-TOCSY correlations (Table 1).

Assignment of the remainder of partial structure b employed COSY and TOCSY data to establish the proton spin systems, HSQC correlations to confirm the sites of oxygenation or nitrogen substitution, and HMBC data to define the locations of the non-protonated olefinic carbons (C-25 and C-29). An HMBC correlation from the C-42 methyl protons to C-34 helped to establish the C-33 to C-34 connectivity, since no vicinal coupling was observed between H-33 and H-34. An HMBC correlation between H-34 and a carbonyl resonance (δ 172.6) in substructure a revealed that chondropsin A (1) incorporated a macrocyclic ring, which resulted from esterification between a carbonyl in fragment a and the C-34 oxygen substituent. The downfield chemical shift of H-34 (δ 5.26) supported the assignment of an ester linkage at this position. The substitution of a nitrogen atom on C-43 was indicated by its $^{13}$C NMR chemical shift (δ 53.7) and by proton-proton coupling between H-43 (δ 4.15) and an amide NH (δ 7.55, H-44). HMBC correlations from H-43 and H-44 to the C-45 carbonyl (δ 176.8) confirmed the presence of an amide at this position. Thus, partial structure b was joined by amide bonds to fragments a and c, and it formed a macrocycle via esterification to a carbonyl in a.

Partial structure c consisted of a 15-carbon chain that contained one olefin, one nitrogen substituent and numerous methyl and hydroxyl substituents. Data from COSY and TOCSY experiments established the connectivities of the two major proton spin systems in c. Proton resonances associated with the adjacent C-48, C-49 methylene pair were in a heavily overlapped region of the NMR spectrum, and thus difficult to interpret. However, HMBC and HSQC-TOCSY correlations unambiguously defined the location of these methylene groups. The position of the $\Delta^{52}$ olefin was established by HMBC correlations from H-51 to the C-52 and C-53 olefinic carbons, and by coupling between H-53 and H-54. The presence of a nitrogen attached to C-56 was revealed by the $^{13}$C chemical shift (δ 53.6), and coupling between H-56 (δ 4.08) and the amide proton H-57 (δ 7.58).

Characteristic $^1$H and $^{13}$C NMR signals indicated that fragment d contained an α,β-unsaturated amide, a ketone, a methyl ester, and two gem dimethyl groups. Structural assignment of d was facilitated by analysis of proton-proton couplings and heteronuclear correlation data. HMBC correlations from H-56, H-57, H-59, and H-60 to the C-58 carbonyl (δ 165.9) established that d was joined to substructure c via an unsaturated amide linkage. Placement of a gem dimethyl substituent at C-61 followed from HMBC correlations between the two methyl groups and C-60 and the C-62 ketone resonance (δ 214.7). Additional HMBC correlations from both H-63 and the C-79 methyl protons to C-62 established that the C-63 methine was also situated α to the ketone. The position of the second gem dimethyl group was defined by HMBC correlations from the C-80 and C-81 methyl protons to C-64 (δ 77.2), C-65 (δ 46.7), and C-66 (δ 178.0), while the methyl ester was defined by a correlation from the singlet methyl protons (δ 3.63) to the C-66 ester carbonyl.

The only remaining unassigned NMR resonances, which consisted of a methylene, an oxymethine group, an ester carbonyl and a carboxylic acid moiety, were assigned to a malic acid residue (substructure e). However, it was not possible to define the relative position of the ester and carboxylic acid moieties within e based on HMBC or NOE correlation data. While the orientation of attachment of e remained ambiguous, its position within chondropsin A (1) was clearly established. An HMBC correlation between H-32 (δ 4.90) and the ester carbonyl (δ 172.8) in e revealed that the malic acid residue was esterified to the C-32 oxygen substituent in substructure b.

Figure 2:
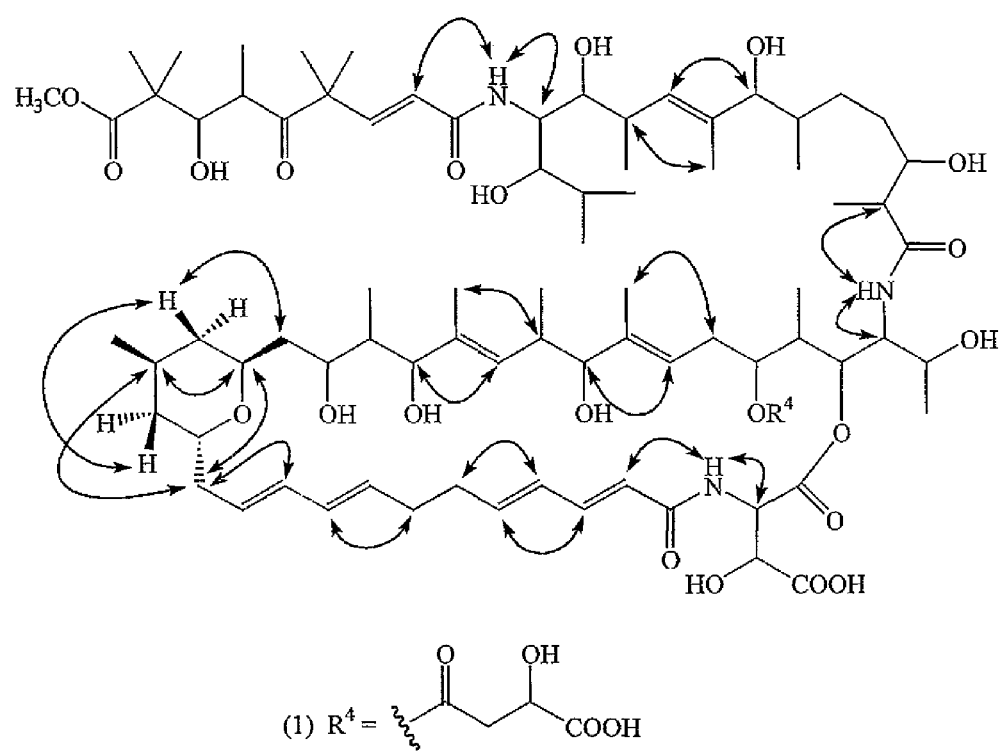
FIG. 2 illustrates key NOESY correlations in chondropsin A.
Figure 2:
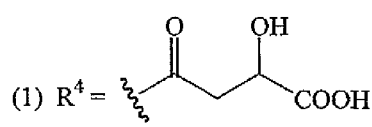

The geometries of the olefinic bonds in (1) were assigned as all trans based on a combination of proton coupling constant analyses and observed NOE interactions (FIG. 2). The $J_{5,6}$, $J_{7,8}$, $J_{11,12}$, $J_{13,14}$, and $J_{59,60}$ vicinal coupling constants of 15.2, 15.0, 14.9, 14.9, and 15.4 Hz, respectively, were indicative of Z double bonds. A trans configuration for $\Delta^{25}$ was established by an NOE observed between H-26 and H-24, and one between the C-39 vinyl methyl protons and the H-27 allylic methine proton. Similar analyses of NOE interactions about the $\Delta^{29}$ and $\Delta^{52}$ double bonds (FIG. 2) also revealed trans geometries. The relative stereochemistry of the tetrahydropyran ring substituents in (1) was also deduced from NOE data. One of the H-15 protons ($\delta$ 2.79) exhibited strong NOE interactions with both H-18, and H-20. This indicated that C-15, H-18 and H-20 all shared a common 1,3-diaxial orientation about the tetrahydropyran ring. All other NOE interactions detected among the ring substituents, including a correlation between H-18 and H-20, supported this assignment.

Initially, our efforts to define the relative position of the ester and carboxylic acid functionalities in substructures a and e in chondropsin A (1) were inconclusive. Thus, extensive spectral characterization and the complete assignment of NMR resonances for the bis methylated derivative (3) were undertaken. The specific HMBC correlations that were required for assignment of the carbonyls in substructures a and e were still lacking in (3), however NOE data proved somewhat helpful. The $^1$H NMR spectrum of compound (3) provided two new O-methyl singlets ($\delta$ 3.71 and 3.67) in addition to the C-66 methyl ester ($\delta$ 3.63). The methyl resonance at $\delta$ 3.71 showed a strong NOE interaction with the H-35 oxymethine proton in a, which indicated that this new O-Me group was attached to C-36. Thus, in chondropsin A (1) C-36 exists as a free carboxylic acid and C-1 is the ester carbonyl linked to the oxygen on C-34. Similar NOE studies failed to differentiate the carbonyl groups in fragment e.

The orientation of substructure e was ultimately assigned by comparing the NMR spectral data of this residue in (1) with spectral data from synthetic monomethyl esters of L-malic acid. The NMR data for (1) showed significantly closer correspondence to the C-4 methyl ester derivative of L-malic acid than to the C-1 derivative. In particular, the chemical shifts of H-2' ($\delta$ 4.53) and H-3' ($\delta$ 2.60 and 2.76) in (1) were consistent with those of the oxymethine ($\delta$ 4.52) and methylene ($\delta$ 2.63 and 2.77) protons of the C-4 monomethyl ester derivative of L-malic acid. Resonances recorded for the oxymethine and methylene protons of the C-1 methyl ester derivative were $\delta$ 4.49, and $\delta$ 2.65 and 2.83, respectively. Thus, attachment of the malic acid residue e was assigned as in (1).

Negative ion FARMS analysis of chondropsin B (2) provided a pseudomolecular ion at m/z 1471.0 which corresponded to [M-H]$^-$. Positive ion HRFABMS of a CsI-doped sample showed an adduct [M+Cs]$^+$ which contained one Cs atom (m/z 1604.8199), accountable to $C_{79}H_{129}N_3O_{22}Cs$. The molecular formula of (2) thus differed from that of chondropsin A (1) by a lack of $C_4H_4O_4$. The NMR data for (2) were very similar to those of (1), with a few notable exceptions. Resonances assigned to the H-2' oxymethine and H-3' methylene protons in (1) were absent in the $^1$H NMR spectra of (2). In addition, the signal for H-32 appeared upfield at $\delta$ 3.52 for (2), in contrast to the corresponding $\delta$ 4.90 for (1). In the $^{13}$C NMR spectrum of (2), signals previously assigned to C-1' through C-4' of the malic acid residue were also missing. An independent assignment of the NMR spectral data (Table 2) and a complete structural elucidation confirmed that chondropsin B (2) is identical to (1), except for the lack of the malic acid side-chain at C-32 in (1). The $^1$H and $^{13}$C NMR data for chondropsin B (2) in DMF-d$_7$ are shown in Table 2, below.

TABLE 2

| Position | $\delta_H$ Mult. (J, Hz) | $\delta_C$ Mult.$^a$ |
|---|---|---|
| 1 | — | 172.6 s |
| 2 | 5.03 m | 55.4 d |
| 3 | 7.99 m | — |
| 4 | — | 167.0 s |
| 5 | 6.27 d (14.5) | 124.1 d |
| 6 | 7.16 dd (11.5, 14.5) | 141.2 d |
| 7 | 6.30 dd (11.5, 14.5) | 129.9 d |
| 8 | 6.15 m | 142.3 d |
| 9 | 2.31 m | 34.4 t$^b$ |
| 10 | 2.16 m | 32.9 t |
| 11 | 5.69 m | 131.4 d |
| 12 | 6.17 d (14.9) | 131.8 d |
| 13 | 6.17 m (14.9) | 132.1 d |
| 14 | 5.69 m | 132.1 d |
| 15 | 2.01 m, 2.79 m | 34.5 t$^b$ |
| 16 | 4.00 m | 72.3 d |
| 17 | H$\beta$ 1.26 m, H$\alpha$ 1.47 m | 38.0 t |
| 18 | 1.86 m | 26.0 d |
| 19 | H$\beta$ 0.80 m, H$\alpha$ 1.51 m | 41.7 t |
| 20 | 3.69 m | 65.9 d |
| 21 | 1.24 m, 1.46 m | 43.1 t |
| 22 | 4.26 m | 66.0 d |
| 23 | 1.46 m | 41.8 d |
| 24 | 3.87 d (9.0) | 80.2 d |
| 25 | — | 138.4 s |
| 26 | 5.13 m | 132.5 d |
| 27 | 2.53 m | 36.6 d |
| 28 | 3.55 m | 82.8 d |
| 29 | — | 137.4 s |
| 30 | 5.34 m | 126.5 d |
| 31 | 2.23 m, 2.30 m | 32.4 t |
| 32 | 3.52 m | 69.2 d |
| 33 | 1.80 m | 38.9 d |
| 34 | 5.26 m | 77.6 d |
| 35 | 4.87 br s | 72.1 d |
| 36 | — | 171.8 s |
| 37 | 0.87 d (6.0) | 22.8 q |
| 38 | 0.62 d (7.0) | 9.7 q |
| 39 | 1.62 s | 11.2 q |
| 40 | 0.71 d (7.0) | 17.9 q |
| 41 | 1.57 s | 11.4 q |
| 42 | 0.92 d (8.0) | 9.4 q |
| 43 | 4.18 m | 53.7 d |
| 44 | 7.61 m | — |
| 45 | — | 176.9 s |
| 46 | 2.58 m | 46.9 d |
| 47 | 3.52 m | 73.9 d |
| 48 | 1.47 m | 33.3 t |
| 49 | 1.21 m | 29.9 t |
| 50 | 1.55 m | 36.3 d |
| 51 | 3.54 m | 83.2 d |
| 52 | — | 137.2 s |
| 53 | 5.50 d (9.5) | 129.5 d |
| 54 | 2.68 m | 35.4 d |
| 55 | 3.77 m | 74.7 d |
| 56 | 4.09 m | 53.8 d |
| 57 | 7.61 m | — |
| 58 | — | 165.9 s |
| 59 | 6.38 d (15.5) | 124.6 d |
| 60 | 6.88 d (15.5) | 146.7 d |
| 61 | — | 51.3 s |
| 62 | — | 214.7 s |
| 63 | 3.22 m | 44.7 d |
| 64 | 4.05 m | 77.2 d |
| 65 | — | 46.7 s |
| 66 | — | 178.0 s |
| 67 | 3.78 m | 69.2 d |
| 68 | 1.12 m | 21.6 q |
| 69 | 1.14 d (7.0) | 15.7 q |
| 70 | 0.95 d (7.0) | 16.0 q |
| 71 | 1.48 s | 11.8 q |
| 72 | 1.01 d (6.5) | 18.1 q |
| 73 | 3.61 m | 75.7 d |

TABLE 2-continued

| Position | $\delta_H$ Mult. (J, Hz) | $\delta_C$ Mult.[a] |
|---|---|---|
| 74 | 1.48 m | 31.5 d |
| 75 | 0.87 d (6.0) | 19.6 q |
| 76 | 0.94 d (7.0) | 20.2 q |
| 77 | 1.21 s | 23.8 q[c] |
| 78 | 1.27 s | 23.9 q[c] |
| 79 | 0.77 d (6.5) | 15.4 q |
| 80 | 1.11 s | 17.7 q |
| 81 | 1.18 s | 25.3 q |
| OCH$_3$ | 3.63 s | 51.8 q |

[a]Multiplicity determined using the DEPT pulse sequence.
[b,c]Assignments may be interchanged.

Example 3

This example illustrates the general procedure for obtaining the activity profile of compounds of the present invention using the NCI 60 cell-line screen.

In this example, chondropsin A was tested as follows. The compound was tested in the NCI 60 cell-line screen as described in detail in Boyd and Paull, *Drug Dev. Res.*, 34, 91-109 (1995); and Monks et al., *J. Natl. Cancer Inst.*, 83, 757-766 (1991). Briefly, a stock solution of the compound was prepared initially in dimethylsulfoxide at 400× the desired final highest test concentrations and stored at −70° C. until use. The final highest test concentrations studied in this example varied between $10^{-5}$ and $10^{-8}$ molar. At the time of screening, an aliquot of the thawed stock was diluted with complete medium containing 50 µg/ml gentamycin to give a concentration of 2× the desired final highest test concentration. Four additional 10-fold serial dilutions were then made to provide a total of five concentrations, spanning a 4-$\log_{10}$ concentration range. One hundred µl aliquots of these intermediate dilutions were immediately added to the appropriate microtitre wells, each already containing the appropriate numbers and types of cells in 100 µl of culture medium, resulting in the desired five final concentrations.

The 60 cell lines used, and the respective inoculation densities, were as described in Boyd and Paull, *Drug Dev. Res.*, 34, 91-109 (1995), and Monks et al., *J. Natl. Cancer Inst.*, 83, 757-766 (1991). Following the compound additions, the plates were incubated for 48 h at 37° C. under a 5% CO$_2$/air atmosphere and 100% humidity. Then, adherent cells (all lines except the leukemia) were fixed in situ by gentle addition of cold trichloroacetic acid (50 µl of 50% w/v) and incubated for 60 min at 4° C. Supernatants were discarded, and plates were washed five times with deionized water and air dried. Sulforhodamine B solution (SRB; 100 µl at 0.4% w/v in 1% acetic acid) was added to each plate, followed by further incubation for 10 min at room temperature. Excess unbound dye was then removed by washing five times with 1% acetic acid, followed by air drying. The bound stain in each well was solubilized by addition of 100 µl of 10 mM unbuffered Tris base; this was followed by a determination of optical densities (515 nm) on an automated plate reader. For suspension cell cultures (the leukemias), the method was the same, except that, at the end of the drug incubation period, the settled cells were fixed in situ to the bottoms of the microtitre wells by gentle addition of 50 µl of 80% trichloroacetic acid. Appropriate control wells were included in the test plate format (Monks et al., *J. Natl. Cancer Inst.*, 83, 757-766 (1991)) to allow subtraction of background optical densities, drug-blank corrections, and a determination of cell densities at time 0 (the time at which compounds are added).

Figure 3A:
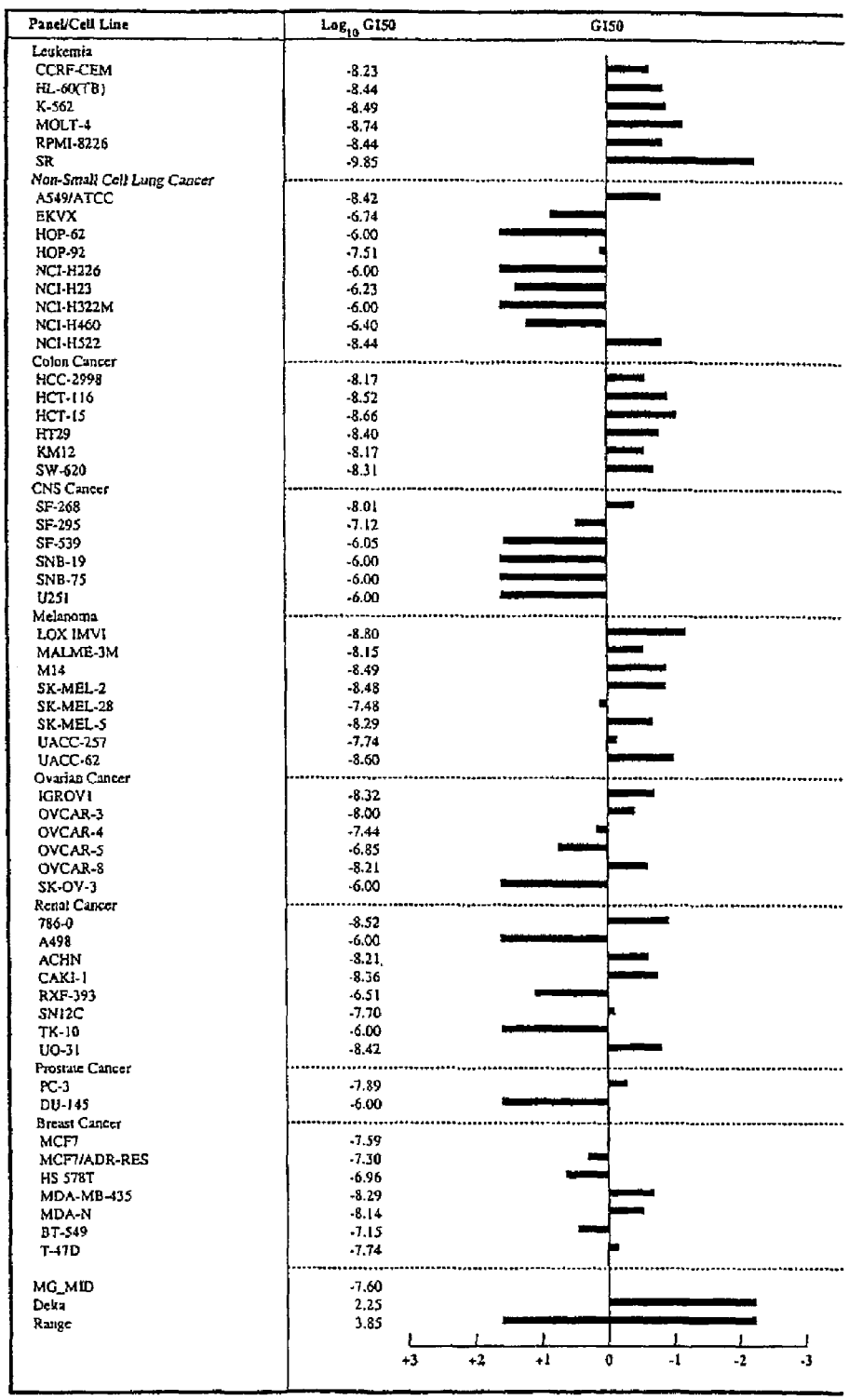
FIG. 3A illustrates the $GI_{50}$-based mean-graph "fingerprint" of chondropsin A in the National Cancer Institute (NCI) 60 cell-line screen.
Figure 3B:
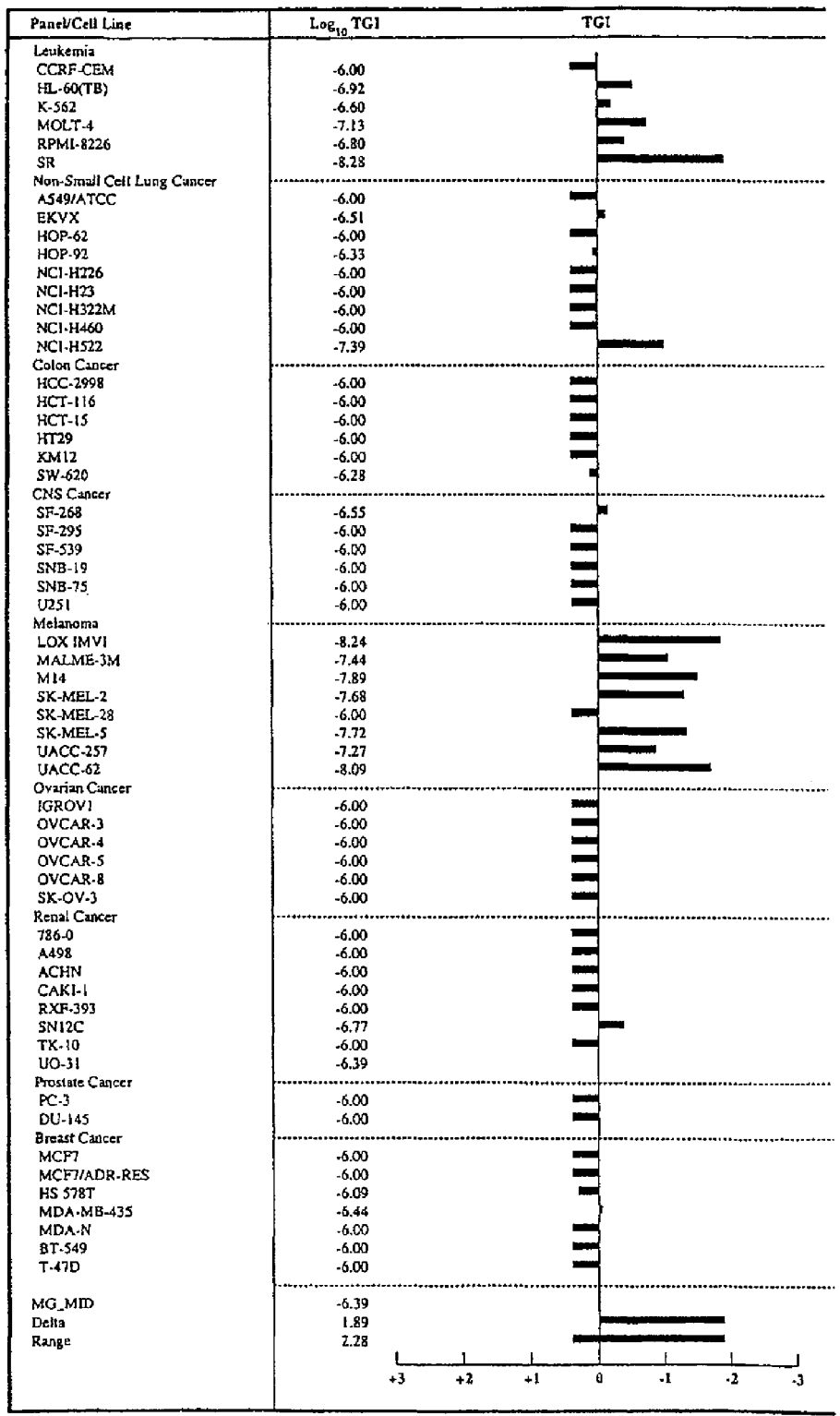
FIG. 3B illustrates the TGI-based mean-graph "fingerprint" of chondropsin A in the NCI 60 cell-line screen.

The quadruplicate testing of pure chondropsin A in the NCI 60 cell-line screen gave the characteristic GI$_{50}$-based and TGI-based mean-graph "fingerprints" in the NCI 60-cell screen exemplified in FIGS. 3A and 3B. The following averaged, individual negative $\log_{10}$ GI$_{50}$ values shown along with the respective subpanel and cell-line identifiers were recorded for chondropsin A: (Leukemia) CCRF-CEM (8.23), HL-60-TB (8.44), K-562 (8.49), MOLT-4 (8.74), RPMI-8226 (8.44), SR (9.85); (Lung) A549/ATCC (8.92), EKVX (6.74), HOP-62 (6.00), HOP-92 (7.51), NCI-H226 (6.00), NCI-H23 (6.23), NCI-H322M (6.00), NCI-H460 (6.40), NCI-H522 (8.44); HCC-2998 (8.17), HCT-116 (8.52), HCT-15 (8.66), HT29 (8.40), KM12 (8.17), SW-620 (8.31); (Brain) SF-268 (8.01), SF-295 (7.12), SF-539 (6.05), SNB-19 (6.00), SNB-75 (6.00), U251 (6.00); (Melanoma) LOX-IMVI (8.80), MALME-3M (8.15), M14 (8.49), SK-MEL-2 (8.48), SK-MEL-28 (7.48), SK-MEL-5 (8.29), UACC-257 (7.74), UACC-62 (8.60); (Ovary) IGROVI (8.32), OVCAR-3 (8.00), OVCAR-4 (7.44), OVCAR-5 (6.85), OVCAR-8 (8.21), SK-OV-3 (6.00); (Kidney) 786-0 (8.52), A498 (6.00), ACHN (8.21), CAKI-1 (8.36), RXF-393 (6.51), SN-12C (7.70), TK-10 (6.00), UO-31 (8.42); (Prostate) PC-3 (7.89), DU-145 (6.00); [Breast] MCF-7 (7.59), MCF-7-ADR-RES (7.30), HS-578T (6.96), MDA-MB-435 (8.29), MDA-N (8.14), BT-549 (7.15), T-47D (7.74).

GI$_{50}$ and TGI-COMPARE analyses of the full data set obtained from the screening of chondropsin A revealed that the compound gave a striking pattern of differential cytotoxicity in the NCI 60 cell-line screen that is characteristic of compounds of the present invention (e.g., Pearson correlation coefficients greater than or equal to 0.7-0.8) but unlike that of any known conventional anticancer drug class. COMPARE pattern-recognition analyses of the mean graph profile of chondropsin A did not reveal any significant correlation to the profiles of known anticancer compounds contained in the NCI's standard agents database. The mean panel GI$_{50}$ concentration of chondropsin A was approximately 25 nM, and the range of differential sensitivity among the 60 cell-lines comprising the NCI panel was about $10^3$ or greater.

Example 4

This example demonstrates the vacuolar-type (H+)-ATPase inhibitory activity of particular compounds of the present invention.

The NCI 60 cell-line in vitro screen was employed to obtain a mean-graph "fingerprint" of a desired mechanistic prototype compound, then using a computer-based search algorithm called COMPARE, to search a database of mean-graph "fingerprints" of structurally unrelated compounds to thereby identify compounds with fingerprints very similar, if not indistinguishable, from that of the selected prototype (or "seed"). The degree of similarity is determined by calculation of a COMPARE correlation coefficient, which can vary from a lowest value of zero (which indicates no correlation) to a highest value of one (which indicates a perfect correlation). A high COMPARE correlation (i.e., indicating a high degree of similarity) between the mean-graph "fingerprints" of different compounds indicates that the compounds act on the same or similar molecular target and therefore share essentially the same or similar mechanism of biological activity. In practical terms, a COMPARE correlation coefficient of about 0.9 or higher indicates that, within the limits of experimental error of the screening process, the mean-graph "fingerprints" of the compared compounds are essentially identical or indistinguishable and, therefore, that the compounds act on the same molecular target. For pertinent background on the NCI 60 cell-line screen and the method and applications of COMPARE, see Boyd, In: *Current Therapy in Oncology* (Niederhuber, J. E., ed) Philadelphia: B.C. Decker, 1993, pp. 11-22; Boyd and Paull, *Drug Dev. Res.,* 34, 91-109, 1995; Paull et al., In: *Cancer Chemotherapeutic Agents*, Washington, D.C.: Am. Chem. Soc. Books, 1995, pp. 11-45.

One of the most potent known vacuolar-type (H+)-ATPase inhibitors, lobatamide A (see, e.g., Boyd, PCT International Patent Application No. PCT/US00/05582), was selected as the mechanistic prototype (or "seed") to use in a COMPARE analysis for purposes of this example. Other known vacuolar-type (H+)-ATPase inhibitors, bafilomycin $A_1$, concanamycin A and salicylihalamide A were selected for use as additional "positive controls." For pertinent background on concanamycins and bafilomycins, see Bowman et al., *Proc. Natl. Acad. Sci. USA,* 85, 7972-7976 (1988); Dröse et al., *Biochemistry,* 32, 3902-3906 (1993); Dröse and Altendoif, J. Exp. *Biol.,* 200, 1-8 (1997). For pertinent background on lobatamide A and salicylihalamide A, see Boyd, PCT International Patent Application No. PCT/US00/05582.

In the present example, authentic, well-characterized and documented reference samples of concanamycin A and bafilomycin $A_1$ were obtained from a commercial supplier (Kamiya Biochemical Company, Tukwila, Wash.). Salicylihalamide A and lobatamide A were obtained as described by Boyd, PCT International Patent Application No. PCT/US00/05582.

The aforementioned "seed" compound, the other positive control compounds, and the test compound were each formulated in DMSO and complete medium, and the resulting compositions were subjected contemporaneously to the NCI 60 cell-line testing procedure as described in Example 3. Each compound was tested in quadruplicate using an upper concentration limit of $10^{-6}$ molar, and 5 $\log_{10}$ dilutions. Resulting data for each compound were used to construct the corresponding mean-graph "fingerprints," and a COMPARE correlation analysis was performed as described further below.

The $GI_{50}$, TGI and $LC_{50}$ mean-graph "fingerprints," respectively, of the mechanistic prototype (or "seed") compound, lobatamide A, were illustrated previously in Boyd, PCT International Patent Application No. PCT/US00/05582. The database that was used in this example, and that was searched using the lobatamide A "seed" comprised, in addition to the mean-graph "fingerprints" obtained from the contemporaneous testing of the aforementioned compounds (i.e., the selected "seed" compound, positive controls and test compound), more than 8000 mean-graph "fingerprints" from the prior testing of structurally diverse pure compounds. The database also comprised the mean-graph "fingerprints" obtained from crude extracts and partially purified fractions thereof, unrelated to the "seed" compound, or to the positive control or test compounds of the present invention, or to extracts or fractions having any known or suspected content of any of the aforementioned compounds.

As appropriate for this demonstration, the TGI mean-graph, derived from the contemporaneous testing of lobatamide A, was used as the "seed" to search against the TGI mean-graphs contained in the aforementioned database, and as the basis for calculation of the COMPARE coefficients. The $GI_{50}$ mean-graphs of each compound tested in the present study were used for the calculation of mean panel $GI_{50}$ values. Table 3 summarizes the TGI-COMPARE correlation coefficients from the testing of lobatamide A, concanamycin A, bafilomycin $A_1$, salicylihalamide A and chondropsin A in the NCI 60 cell-line screen. The mean-panel $GI_{50}$ values are also shown in Table 3. The COMPARE correlations shown in Table 3 were performed using the TGI mean-graph of lobatamide A as the "seed."

TABLE 3

| Compound | TGI-COMPARE Correlation Coefficient | Mean-Panel $GI_{50}$ × $10^{-8}$M (±S.D.) |
|---|---|---|
| Lobatamide A* | 1.00 | 0.56 (0.09) |
| Concanamycin A* | 0.94 | 0.11 (0.03) |
| Bafilomycin $A_1$* | 0.92 | 1.02 (0.71) |
| Salicylihalamide A* | 0.93 | 4.97 (1.03) |
| Chondropsin A | 0.92 | 2.56 (0.77) |

*Comparative example.

As shown by the expected perfect correlation (COMPARE correlation coefficient, 1.0) of the seed compound (lobatamide A) with itself, the computer-based algorithm analysis was working properly and precisely for this demonstration. Moreover, the other positive control compounds, concanamycin A, bafilomycin $A_1$, and salicylihalamide A showed correlations with the seed compound of approximately 0.90 or greater, confirming that this analysis could correctly identify compounds which, although structurally distinct from the seed, nonetheless share the same molecular target (i.e., in this instance, vacuolar-type (H+)-ATPase). Most notably, all of the selected test compounds including the exemplary compound, chondropsin A, in this example showed, in reference to the "seed," COMPARE correlation coefficients of at least 0.92 or higher, thus demonstrating that the molecular target of all of the compounds, including chondropsin A, is likewise vacuolar-type (H+)-ATPase. The compounds of the present invention may exhibit a range of relative absolute potencies against vacuolar-type (H+)-ATPase.

Example 5

This example demonstrates the vacuolar-type (H+)-ATPase inhibitory activity of exemplary compounds of the present invention.

The V-ATPase inhibitory assays were performed on representative compound(s) of the present invention using non-mammalian or mammalian (e.g., bovine cromaffin granule) V-ATPases as described by Bowman et al., *Proc. Natl. Acad. Sci. USA,* 85, 7972-7976, 1988. The results are shown in Table 4.

TABLE 4

| Compound | V-ATPase CGM* | (Ki, nM) NCVM** | Ratio GCM/NC |
|---|---|---|---|
| Bafilymycin $A_1$*** | 6.0 | 13 | 0.5 |
| Concanamycin A*** | 6.0 | 4.0 | 1.5 |
| Salicylihalamide A*** | 6.5 | >10,000 | <0.0007 |
| Chondropsin A | >10,000 | 800 | >13 |
| Chondropsin B | 6,000 | 200 | 30 |
| Chondropsin C | 3,000 | 80 | 38 |
| Chondropsin D | >10,000 | 140 | >71 |
| Chondropsin A, dimethyl ester | 500 | 50 | 10 |
| Chondropsin A, 73-deoxy | 3,000 | 100 | 30 |

*CGM, Chromaffin Granule Membrane V-ATPase
**NCVM, *Neurospora crassa* vacuolar membrane V-ATPase
***Comparative example The results shown in Table 4 show a striking contrast in the specificity profiles of representative compounds of the present invention, as compared to the other known classes of inhibitors, such as bafilymycins, concanamycins and benzolactone enamides (e.g., salicylihalamide A) (Boyd et al., J. Pharmacol, Exp. Therap. 297: 114-129). Thus, the compounds of the present invention represent an entirely new class of V-ATPase inhibitors.

The bafilomycin-sensitive vacuolar-type (H+)-ATPase activities of exemplary compounds of the present invention also can be measured using partially purified membrane vesicle preparations from human osteoclastoma cells (hOc), human renal cortical cells (hK), or macrophage cells (J774). The vesicles can be prepared by appropriate adaptations of methods described in Gagliardi et al., *J. Med. Chem.*, 41, 1568-1573 (1998); and Gagliardi et al., *J. Med. Chem.*, 41, 1883-1893 (1998).

Vacuolar-type (H+)-ATPase assays are typically performed in the presence of oligomycin (5 μg/ml) and vanadate (1 mM) as inhibitors of F- and P-ATPases, respectively. A colorimetric method may be used to quantitate the residual bafilomycin-sensitive vacuolar-type (H+)-ATPase activity (see Chan et al., *Anal. Biochem.*, 157, 375-380 (1986)). The assay measures the release of inorganic phosphate from ATP at 37° during 30 min of incubation. The reaction is initiated by the addition of $MgSO_4$ (5 M final concentration).

Example 6

This example demonstrates a method of obtaining exemplary compounds of the present invention.

An aqueous extract (27.5 g) of *Ircinia ramosa* collected in Australia was fractionated on $C_4$ reversed-phase media, Sephadex LH-20, and $C_{18}$ HPLC (eluted with a 45-100% gradient of $CH_3CN$ in $H_2O$ with 0.1% TFA) to give chondropsin A (FIG. 1A, compound (1)) (1 mg) and 73-deoxychondropsin A (5 mg) (FIG. 1A, compound (4)). 73-deoxychondropsin A was obtained as a white powder; $[\alpha]_D$ +2.0 (c 0.3, MeOH); W (MeOH) $\lambda_{max}$ (log ε) 216 (4.62), 226 (4.61), 261 (4.56) nm; IR $\upsilon_{max}$ (film) 3500-3200, 1660, 1620, 1532, 1204, 1138, 998 cm$^{-1}$; $^1$H and $^{13}$C NMR, see Table 5; HRFABMS (CsI-doped) obs. [M+Cs]$^+$, m/z 1704.8308, $C_{83}H_{133}CsN_3O_{25}$ requires 1704.8279. HRFABMS established the molecular formula of (4) as $C_{83}H_{133}N_3O_{25}$, which only differed from (1) by a lack of one oxygen atom. The $^1$H and $^{13}$C NMR spectra of (4) (Table 5) were virtually superimposable with those of (1). The only significant spectral differences between the two compounds occurred in a region centered around C-73. It was apparent that the oxymethine at C-73 in (1) was replaced with a methylene in (4). HMBC correlations observed from H-53 (δ 5.42) and NH-57 (δ 7.62) to C-55 (δ 78.2) confirmed the presence of a C-55 oxymethine group in (4), while an HMBC correlation from H-55 (δ 3.36) to C-73 (δ 40.3) established the position of the new methylene group. A DEPT experiment confirmed that the carbon at δ 40.3 had two attached protons and COSY correlations from H-56 (δ 4.07) to the heavily overlapped region of the $H_2$-73 protons (δ 1.46 and 1.54) were consistent with the presence of a methylene at C-73. Treatment of (4) with diazomethane provided a bis methyl ester derivative (MNa$^+$, m/z 1622.9) (FIG. 1A, compound (5)) and data from a comprehensive set of 2-D NMR experiments with (4) verified that the only difference between (1) and (4) was at C-73.

TABLE 5

| Pos.[a] | $\delta_C$ Mult.[b] | $\delta_H$ Mult. (J in Hz) |
|---|---|---|
| 1 | 171.9 s | |
| 2 | 55.5 d | 5.15 m |
| 3 | | 7.91 d (9.5) |
| 4 | 167.5 s | |
| 5 | 124.4 d | 6.30 d (15.0) |
| 6 | 140.7 d | 7.14 dd (15.0, 10.5) |
| 7 | 129.8 d | 6.28 dd (15.0, 10.5) |
| 8 | 142.1 d | 6.12 m |
| 9 | 34.5 t | 2.29 m |
| 10 | 33.0 t | 2.15 m |
| 11 | 131.3 d | 5.70 m |
| 12 | 131.9 d | 6.17 d (14.9) |
| 13 | 132.0 d | 6.17 d (14.9) |
| 14 | 132.0 d | 5.67 m |
| 15 | 34.6 t | 2.03 m, 2.79 m |
| 16 | 72.3 d | 4.00 m |
| 17 | 37.9 t | Hβ 1.27 m, Hα1.48 m |
| 18 | 25.9 d | 1.85 m |
| 19 | 41.7 t | Hβ 0.82 m, Hα1.52 m |
| 20 | 65.9 d | 3.69 m |
| 21 | 42.9 t | 1.24 m, 1.46 m |
| 22 | 66.0 d | 4.25 m |
| 23 | 41.8 d | 1.45 m |
| 24 | 80.2 d | 3.86 d (9.0) |
| 25 | 138.0 s | |
| 26 | 132.1 d | 5.12 m |
| 27 | 36.4 d | 2.50 m |
| 28 | 82.4 d | 3.51 d (8.1) |
| 29 | 138.7 s | |
| 30 | 123.4 d | 5.22 t (6.5) |
| 31 | 31.8 t | 2.05 m, 2.45 m |
| 32 | 73.1 d | 4.85 m |
| 33 | 38.6 d | 2.00 m |
| 34 | 77.0 d | 5.10 m |
| 35 | 72.1 d | 4.82 bs |
| 36 | 171.8 s | |
| 37 | 22.8 q | 0.87 d (6.6) |
| 38 | 9.8 q | 0.62 d (7.0) |
| 39 | 11.2 q | 1.57 s |
| 40 | 18.1 q | 0.65 d (6.0) |
| 41 | 11.3 q | 1.55 s |
| 42 | 9.7 q | 1.03 d (7.0) |
| 43 | 53.3 d | 4.15 m |
| 44 | | 7.50 d (10.0) |
| 45 | 176.7 s | |
| 46 | 47.3 d | 2.54 m |
| 47 | 73.5 d | 3.52 m |
| 48 | 33.1 t | 1.48 m |
| 49 | 29.3 t | 1.21 m, 1.47 m |
| 50 | 36.2 t | 1.57 m |
| 51 | 83.1 d | 3.57 m |
| 52 | 137.2 s | |
| 53 | 130.4 d | 5.42 d (9.5) |
| 54 | 35.7 d | 2.64 m |
| 55 | 78.2 d | 3.36 m |
| 56 | 50.4 d | 4.07 m |
| 57 | | 7.62 d (10.0) |
| 58 | 165.4 s | |
| 59 | 124.5 d | 6.31 d (15.5) |
| 60 | 146.8 d | 6.89 d (15.5) |
| 61 | 51.3 s | |
| 62 | 214.7 s | |
| 63 | 44.6 d | 3.20 dq (10.0, 7.0) |
| 64 | 77.2 d | 4.04 d (10.0) |
| 65 | 46.7 s | |
| 66 | 178.0 s | |
| 67 | 69.3 d | 3.78 m |
| 68 | 21.1 q | 1.08 d (6.2) |
| 69 | 15.5 q | 1.13 d (7.0) |
| 70 | 15.8 q | 0.93 d (7.0) |
| 71 | 12.2 q | 1.54 s |
| 72 | 17.8 q | 0.96 d (7.0) |
| 73 | 40.3 t | 1.46 m, 1.54 m |
| 74 | 25.2 d | 1.56 m |
| 75 | 24.4 q | 0.86 d (6.0) |
| 76 | 21.8 q | 0.89 d (6.0) |
| 77 | 23.8 q | 1.20 s |
| 78 | 23.9 q | 1.26 s |
| 79 | 15.3 q | 0.76 d (7.0) |
| 80 | 17.7 q | 1.10 s |

TABLE 5-continued

| Pos.[a] | $\delta_C$ Mult.[b] | $\delta_H$ Mult. (J in Hz) |
|---|---|---|
| 81 | 25.2 q | 1.17 s |
| 1' | 172.6 s | |
| 2' | 68.8 d | 4.52 dd (8.4, 4.0) |
| 3' | 40.2 t | 2.63 m, 2.78 m |
| 4' | 172.9 s | |
| OCH$_3$ | 51.7 q | 3.62 s |

[a]$^1$H and $^{13}$C spectra acquired at 500 and 125 MHz, respectively (DMF-d$_7$).
[b]Multiplicity inferred from the DEPT pulse sequence.

Example 7

This example demonstrates a method of obtaining exemplary compounds of the present invention.

An aqueous extract (37.5 g) of a Philippines collection of *Ircinia* sp. was fractionated in a manner similar to that described in Example 6, to provide 5 mg of chondropsin C (FIG. 1A, compound (6)) as a white powder; [α]$_D$ +2.7 (c 0.3, MeOH); UV (MeOH) λ$_{max}$ (log ε) 222 (4.66), 228 (4.64), 261 (4.58) nm; IR υ$_{max}$ (film) 3500-3200, 1730, 1699, 1630, 1540, 1208, 1199, 1068, 1021, 958 cm$^{-1}$; $^1$H and $^{13}$C NMR see Table 6; HRFABMS (CsI-doped) obs. [M+Cs]$^+$, m/z 1646.8165, C$_{81}$H$_{131}$CsN$_3$O$_{23}$ requires 1646.8224. A molecular formula of C$_{81}$H$_{131}$N$_3$O$_{23}$ was established for compound (6) by HRFABMS. NMR data sets were obtained in DMF-d$_7$, to facilitate spectral comparisons with the other chondropsins, and in CD$_3$OH. This allowed complete assignment of the $^1$H and $^{13}$C NMR resonances for chondropsin C (Table 6).

TABLE 6

| Pos.[a,b] | $\delta_C$ Mult.[c] | $\delta_H$ Mult. (J in Hz) | HMBC |
|---|---|---|---|
| 1 | 172.7 s | | |
| 2 | 56.0 d | 5.15 m | C-1, C-4, C-35, C-36 |
| 3 | | 7.73 d (8.5) | C-2, C-4 |
| 4 | 169.8 s | | |
| 5 | 124.0 d | 6.22 d (15.0) | C-4, C-7 |
| 6 | 142.5 d | 7.13 dd (15.0, 11.0) | C-4 |
| 7 | 130.1 d | 6.27 dd (15.0, 11.0) | C-8, C-9 |
| 8 | 143.6 d | 6.15 m | C-6, C-9, C-10 |
| 9 | 35.6 t | 2.30 m | C-8, C-10 |
| 10 | 33.6 t | 2.13 m, 2.19 m | |
| 11 | 131.9 d | 5.70 m | |
| 12 | 132.4 d | 6.17 bd (15.0) | C-10, C-14 |
| 13 | 132.6 d | 6.14 bd (15.0) | C-14, C-15 |
| 14 | 132.9 d | 5.67 m | C-13, C-16 |
| 15 | 35.2 t | 2.06 m, 2.78 m | |
| 16 | 73.0 d | 4.06 m | C-20[d] |
| 17 | 38.2 t | Hβ 1.31 m, Hα 1.52 m | C-15, C-16 |
| 18 | 26.6 d | 1.87 m | |
| 19 | 41.8 t | Hβ 0.86 m, Hα 1.53 m | |
| 20 | 66.7 d | 3.68 m | |
| 21 | 42.7 t | 1.23 m, 1.50 m | C-19, C-20 |
| 22 | 66.9 d | 4.22 bd (10.5) | C-21, C-24, C-38 |
| 23 | 41.9 d | 1.55 m | |
| 24 | 81.4 d | 3.81 d (9.5) | C-22, C-26, C-39 |
| 25 | 137.9 s | | |
| 26 | 134.6 d | 5.02 m | C-24, C-27, C-40 |
| 27 | 36.3 d | 2.47 m | |
| 28 | 84.1 d | 3.43 d (9.0) | |
| 29 | 138.5 s | | |
| 30 | 124.1 d | 5.20 t (6.5) | C-28, C-41 |
| 31 | 32.7 t | 2.05 m, 2.45 m | C-30, C-32 |
| 32 | 73.7 d | 4.84 m | C-4'[d] |
| 33 | 39.1 | 1.93 m | C-34, C-42 |
| 34 | 78.2 d | 5.06 m | C-1, C-33, C-67 |
| 35 | 72.4 d | 4.85 m | |
| 36 | 172.7 s | | |
| 37 | 22.8 q | 0.89 d (6.5) | C-17, C-18, C-19 |
| 38 | 9.3 q | 0.58 d (7.0) | C-22, C-23, C-24 |
| 39 | 10.7 q | 1.54 s | C-24, C-26 |
| 40 | 17.9 q | 0.57 d (6.5) | C-26, C-27, C-28 |
| 41 | 10.7 q | 1.52 s | C-28, C-29 |
| 42 | 10.0 q | 1.02 d (7.0) | C-32, C-33, C-34 |
| 43 | 54.1 d | 4.11 m | C-45, C-67 |
| 44 | | 7.45 d (10.0) | C-45 |
| 45 | 178.9 s | | |
| 46 | 48.5 d | 2.50 m | C-45, C-47, C-69 |
| 47 | 74.3 d | 3.52 m | |
| 48 | 33.2 t | 1.50 m, 1.54 m | |
| 49 | 29.7 t | 1.18 m, 1.30 m | C-50, C-47 |
| 50 | 36.8 t | 1.61 m | |
| 51 | 84.1 d | 3.66 d (8.0) | C-47, C-52, C-70, C-71 |
| 52 | 137.7 s | | |
| 53 | 131.2 d | 5.36 d (10.0) | |
| 54 | 36.2 d | 2.66 m | |
| 55 | 78.9 d | 3.36 dd (11.0, 5.5) | C-53, C-56, C-72, C-73 |
| 56 | 51.4 d | 4.03 m | |
| 57 | | 7.80 d (10.2) | C-56, C-58 |
| 58 | 167.6 s | | |
| 59 | 124.1 d | 6.10 d (16.0) | C-58, C-61 |
| 60 | 148.6 d | 6.93 d (16.0) | C-58, C-59, C-62, C-77 |
| 61 | 52.0 | | |
| 62 | 217.2 s | | |
| 63 | 45.8 d | 3.16 dq (9.5, 6.5) | C-62, C-64, C-65 |
| 64 | 78.7 d | 3.56 dd (9.5, 2.5) | C-63, C-80, C-81 |
| 65 | 30.1 d | 1.27 m | |
| 67 | 70.2 d | 3.77 m | |
| 68 | 21.8 q | 1.10 d (6.5) | C-43, C-67 |
| 69 | 15.7 q | 1.14 d (6.5) | C-45, C-46, C-47 |
| 70 | 15.9 q | 0.96 d (6.5) | C-49, C-50, C-51 |
| 71 | 12.0 q | 1.53 s | C-51, C-52, C-53 |
| 72 | 17.9 q | 0.98 d (6.5) | C-53, C-54, C-55 |
| 73 | 40.3 t | 1.45 m, 1.48 | |
| 74 | 25.8 d | 1.56 m | |
| 75 | 24.4 q | 0.91 d (7.0) | C-73, C-74, C-76 |
| 76 | 22.0 q | 0.90 d (7.0) | |
| 77 | 23.8 q[e] | 1.25 s | C-60, C-61, C-62 |
| 78 | 23.9 q[e] | 1.28 s | C-60, C-61, C-62 |
| 79 | 15.7 q | 0.87 d (6.5) | C-62, C-64 |
| 80 | 14.3 q | 0.82 d (6.5) | C-64, C-65, C-81 |
| 81 | 20.5 q | 0.94 d (7.0) | C-64, C-65, C-80 |
| 1' | 174.0 s[f] | | |
| 2' | 68.9 d | 4.50 dd (8.4, 4.0) | C-1', C-3', C-4' |
| 3' | 40.1 t | 2.56 m, 2.66 m | C-1', C-2', C-4' |
| 4' | 173.9 s[f] | | |

[a]$^1$H and $^{13}$C spectra were acquired at 500 and 125 MHz, respectively (CD$_3$OH).
[b]To facilitate spectral comparisons, the numbering scheme is the same as that used originally for (1), thus, compound (6) does not contain a C-66.
[c]Multiplicity inferred from the DEPT pulse sequence.
[d]Correlation only observed in DMF-d$_7$.
[e,f]Assignments may be interchanged.

Both the macrocyclic ring and acyclic portions of (6) had NMR signals that corresponded closely with those recorded for compounds (1) and (4). However, the $^{13}$C NMR spectrum of 6 had one less carbonyl resonance, and the OCH$_3$ group seen in (1) and (4) was missing in (6). The C-80 and C-81 gem dimethyl groups in (6) appeared as a pair of doublets, each coupled to a new methine proton (δ 1.27) at C-65. COSY and HMBC correlations confirmed this assignment. Thus, (6) lacked the entire methyl ester functionality that terminated the acyclic chain in (1) and (4). Spectral characteristics of the region around C-73 in (6) closely matched those observed in (4). Data from DEPT, HSQC, COSY and HMBC experiments unambiguously established the presence of a methylene group at C-73, as seen in (4). Additional evidence supporting the structure of (6) included an HMBC correlation from H-34 (δ 5.06) to C-1 (δ 172.7), which confirmed that ring closure of the macrolide was effected via esterification with the C-34 oxygen substituent. Attachment of the malic acid residue at C-32 was established by an HMBC correlation between H-32 and the C-4' ester carbonyl. NOE and coupling constant analyses were consistent with trans geometries for all of the olefins in (6), while a series of 1,3-diaxial NOE interactions defined the relative stereochemistry of the tetrahydropyran ring substituents. Treatment of (6) with diazomethane generated a bis methyl ester derivative (MNa$^+$, m/z 1565.0) (FIG. 1A, compound (7)).

Example 8

This example demonstrates a method of obtaining exemplary compounds of the present invention.

A sample of the frozen sponge material described in Example 1 was subjected to the extraction and chromatographic separation described in Example 1. Repeated $C_{18}$ HPLC eluted with a linear $CH_3CN$—$H_2O$ gradient provided a total of 3.5 mg of chondropsin D (FIG. 1A, compound (8)). Final purification of chondropsin D was achieved by $C_{18}$ reversed-phase HPLC (Dynamax ODS, 10×250 mm, 8 μm; flow rate, 3 mL/min) using a linear $CH_3CN$—$H_2O$ gradient (45:55 to 100:0 over 30 min). A total of 3.5 mg (0.001% wet weight) of chondropsin D was obtained as a white gum, $[\alpha]^{27}_D$-5.0° (c 0.06, MeOH); UV [MeOH] $\lambda_{max}$ (log ϵ) 225 (4.18), 262 (4.01) nm; IR $\upsilon_{max}$ (KBr) 3500-3300, 1680, 1610, 1532, 1200, 1180 cm$^{-1}$; $^1$H and $^{13}$C NMR data see Table 7; FABMS (M+Na)$^+$m/z 1610.9; HRFABMS CsI doped sample, (M-H+2Cs)$^+$ m/z 1852.7283, calcd for $C_{83}H_{132}N_3O_{26}Cs_2$, 1720.8232.

The molecular formula of chondropsin D was established by HRFABMS to be $C_{83}H_{133}N_3O_{26}$, which indicated that it was isomeric with chondropsin A. The IR and UV spectra recorded for chondropsins D and A were virtually identical. A comprehensive set of 1-D and 2-D NMR data for chondropsin D were collected and analyzed. A complete assignment of the $^1$H and $^{13}$C resonances for chondropsin D are shown in Table 7 (DMF-$d_7$). The only apparent structural difference between chondropsins A and D was the position of the ester link in the macrocycle. In chondropsin A an ester bridge was formed between the C1 carbonyl and the oxygen on C-34. The H-34 resonance in chondropsin D was shifted upfield to δ 3.66 (versus δ 5.11 in chondropsin A), which suggested that C-34 was now substituted with a hydroxyl group. In addition, H-67 in chondropsin D was deshielded to δ 5.03 (versus δ 3.78 in chondropsin A), which was consistent with an ester linkage at this position.

TABLE 7

| Pos. | $\delta_C$ Mult.$^a$ | $\delta_H$ Mult. (J in Hz) | HMBC |
|---|---|---|---|
| 1 | 172.6 s | | |
| 2 | 55.9 d | 5.13 dd (9.0, 2.2) | C-35 |
| 3 | | 8.16 d (9.0) | |
| 4 | 167.6 s$^b$ | | |
| 5 | 124.4 d | 6.29 d (15.0) | C-4$^b$ |
| 6 | 140.4 d | 7.11 dd (15.0, 11.0) | C-4$^b$, C-7 |
| 7 | 129.7 d | 6.26 dd (15.0, 11.0) | |
| 8 | 141.6 d | 6.10 m | |
| 9 | 34.0 t$^c$ | 2.25 m | |
| 10 | 32.3 t | 2.18 m | C-12 |
| 11 | 131.5 d | 5.59 dt (15.0, 7.5) | |
| 12 | 132.0 d | 6.12 d | C-10 |
| 13 | 132.1 d | 6.11 m | C-15 |
| 14 | 130.8 d | 5.72 dt (15.0, 8.0) | C-12, C-13 |
| 15 | 34.4 t$^c$ | 2.05 m, 2.72 m | |
| 16 | 73.2 d | 3.87 m | |
| 17 | 37.9 t | Hβ 1.25 m, Hα 1.49 m | |
| 18 | 25.6 d | 1.81 m | |
| 19 | 41.7 t$^d$ | Hβ 0.80 m, Hα 1.50 m | |
| 20 | 66.7 d | 3.72 m | |
| 21 | 42.8 t | 1.44 m, 1.49 m | |
| 22 | 67.7 d | 4.15 bd (10.5) | |
| 23 | 41.9 d$^d$ | 1.49 m | |
| 24 | 80.2 d | 3.91 d (9.5) | C-22, C-23, C-26, C-39 |
| 25 | 137.9 s | | |
| 26 | 130.7 d | 5.27 m | C-24, C-28, C-39 |
| 27 | 36.5 d | 2.61 m | |
| 28 | 81.6 d | 3.71 d (9.0) | C-27, C-29, C-30, C-40 |
| 29 | 140.0 s | — | |
| 30 | 121.5 d | 5.30 m | C-28, C-32, C-41 |
| 31 | 30.1 t | 2.22 m, 2.52 m | |
| 32 | 74.3 d | 5.23 bt (7.0) | C-1' |
| 33 | 38.8 d | 1.82 m | |
| 34 | 72.6 d | 3.50 m | |
| 35 | 72.0 d | 4.73 d (2.0) | |
| 36 | 171.6 s$^b$ | | |
| 37 | 22.8 q | 0.86 d (6.5) | C-17, C-18, C-19 |
| 38 | 10.9 q | 0.71 d (7.0) | C-22, C-23, C-24 |
| 39 | 12.6 q | 1.62 s | C-24, C-25, C-26 |
| 40 | 18.2 q | 0.84 d (6.5) | C-26, C-27, C-28 |
| 41 | 12.0 q | 1.59 s | C-28, C-29, C-30 |
| 42 | 10.1 q | 0.92 d (7.0) | C-32, C-33, C-34 |
| 43 | 53.6 d$^e$ | 4.18 m | |
| 44 | | 7.43 d (9.0) | |
| 45 | 176.6 s | | |
| 46 | 47.2 d | 2.47 m | |
| 47 | 73.6 d | 3.52 m | |
| 48 | 33.2 t | 1.48 m | |
| 49 | 30.1 t | 1.17 m, 1.31 m | |
| 50 | 36.4 t | 1.55 m | |
| 51 | 83.1 d | 3.52 d (8.0) | |
| 52 | 137.3 s | | |
| 53 | 129.6 d | 5.49 d (10.0) | C-51, C-55, C-71 |
| 54 | 35.3 d | 2.67 m | |
| 55 | 74.5 d | 3.76 m | |
| 56 | 53.7 d$^e$ | 4.05 m | C-55, C-58 |
| 57 | | 7.59 d (10.0) | C-58 |
| 58 | 165.9 s | | |
| 59 | 124.7 d | 6.36 d (15.5) | C-58, C-61 |
| 60 | 146.7 d | 6.88 d (15.5) | C-58, C-59, C-62, C-77 |
| 61 | 51.3 s | | |
| 62 | 214.7 | | |
| 63 | 44.4 d | 3.20 dq (9.5, 6.5) | C-62, C-64, C-79 |
| 64 | 77.2 d | 4.03 dd (9.5, 2.5) | |
| 65 | 46.7 s | | |
| 66 | 178.0 s | | |
| 67 | 74.4 d | 5.00 m | |
| 68 | 17.6 q | 1.23 d (6.0) | C-43, C-67 |
| 69 | 15.3 q | 1.12 d (67.0) | C-45, C-46, C-47 |
| 70 | 15.9 q | 0.95 d (7.0) | C-49, C-50, C-51 |
| 71 | 11.7 q | 1.47 s | C-51, C-52, C-53 |
| 72 | 18.1 q | 1.00 d (6.5) | C-53, C-54, C-55 |
| 73 | 75.6 d | 3.60 m | |
| 74 | 31.5 d | 1.48 m | |
| 75 | 19.6 q | 0.87 d (7.0) | C-73, C-74, C-76 |
| 76 | 20.1 q | 0.94 d (7.0) | C-73, C-74, C-75 |
| 77 | 23.8 q | 1.20 s | C-60, C-61, C-62 |
| 78 | 23.7 q | 1.27 s | C-60, C-61, C-62 |
| 79 | 15.3 q | 0.76 d (6.5) | C-62, C-63, C-64 |
| 80 | 17.7 q | 1.11 s | C-64, C-65, C-81 |
| 81 | 25.3 q | 1.17 s | C-64, C-65, C-80 |
| 1' | 174.1 s | | |
| 2' | 68.8 d | 4.52 dd (8.4, 4.0) | C-4' |
| 3' | 40.3 t | 2.67 m, 2.73 m | C-1', C-4' |
| 4' | 173.5 s | | |
| OCH$_3$ | 51.7 q | 3.62 s | C-66 |

$^a$Multiplicity inferred from a DEPT pulse sequence.
$^b$Assignments based on HMBC correlations seen in the bis methyl ester.
$^{c,d,e}$Assignments may be interchanged.

Example 9

This example demonstrates a method of obtaining an exemplary compound of the present invention and demonstrates the cytotoxicity of the compound thus obtained.

A 2.0 mg solution of chondropsin A in pyridine-$d_5$ was kept at room temperature and $^1$H NMR spectra were periodically acquired. Within one day, new $^1$H resonances were observed and these signals gradually increased over time. After 7 days, the pyridine was removed under reduced pressure and the residue was purified by HPLC as described above to give 0.6 mg of a compound that by FABMS, HPLC retention time, $^1$H NMR, and HSQC data, was identical to chondropsin D. Thus, chondropsin D can be prepared from chondropsin A via a base-catalyzed transesterification reaction in which the ester migrates from O-34 to O-67. The characterization of chondropsin D was facilitated by spectral analysis of the product of the corresponding base-catalyzed transesterification reaction of the dimethyl ester of chondropsin A (FIG. 1A, compound (3)), which produced the dimethyl ester of chondropsin D (FIG. 1A, compound (9)). Chondropsin D was evaluated for cytotoxic activity towards melanoma (LOX) and leukemia (MOLT-4) human tumor cell lines in a 2-day in vitro assay, the procedure for which is described in Bokesch et al., *J. Nat. Prod.*, 62, 633-635 (1999). Chondropsin D exhibited IC$_{50}$'s of approximately 10 ng/mL and 250 ng/mL towards the LOX and MOLT-4 cell lines, respectively.

Example 10

This example demonstrates a method of obtaining an exemplary compound of the present invention.

A solution of 0.2 mg chondropsin D in 1.0 mL of MeOH was treated at room temperature with an excess of $CH_2N_2$ in diethyl ether (3.0 mL). The solvent was removed under a stream of $N_2$ and the residue was dissolved in MeOH and purified by $C_{18}$ HPLC (eluted with a linear gradient from 45-100% $CH_3CN$ in $H_2O$ containing 0.1% TFA) to give 0.1 mg of the methylated derivative (FIG. 1A, compound (9)): $^1$HNMR (DMF-$d_7$) data see Table 8; FABMS (M+Na)$^+$ m/z 1638.9, appropriate for $C_{85}H_{137}N_3O_{26}Na$.

TABLE 8

| Pos.[a] | $\delta_C$ | $\delta_H$ Mult. (J in Hz) |
|---|---|---|
| 2 | 55.7 | 5.15 dd (9.0, 2.0) |
| 3 | | 8.30 d (9.0) |
| 5 | 124.7 | 6.29 d (15.0) |
| 6 | 140.7 | 7.15 dd (15.0, 11.0) |
| 7 | 129.5 | 6.23 dd (16.0, 11.0) |
| 8 | 141.7 | 6.07 m |
| 9 | 33.0 | 2.27 m |
| 10 | 32.3 | 2.19 m |
| 11 | 131.4 | 5.60 m |
| 12 | 132.3 | 6.10 d (14.9) |
| 13 | 132.3 | 6.10 d (14.9) |
| 14 | 130.9 | 5.70 m |
| 15 | 34.5 | 2.04 m, 2.68 m |
| 16 | 73.4 | 3.85 m |
| 17 | 37.8 | Hβ 1.27 m, Hα 1.50 m |
| 18 | 25.5 | 1.80 m |
| 19 | 41.7 | Hβ 0.80 m, Hα 1.58 m |
| 20 | 66.5 | 3.77 m |
| 21 | 42.8 | 1.20 m, 1.46 m |
| 22 | 67.3 | 4.20 m |
| 23 | 41.5 | 1.50 m |
| 24 | 80.2 | 3.91 d (9.0) |
| 26 | 130.0 | 5.30 m |
| 27 | 36.7 | 2.61 m |
| 28 | 81.1 | 3.74 m |
| 30 | 121.2 | 5.30 m |
| 31 | 30.8 | 2.22 m, 2.45 m |
| 32 | 74.9 | 5.24 bt (6.5) |
| 33 | 39.5 | 1.87 m |
| 34 | 72.3 | 3.50 m |
| 35 | 72.0 | 4.71 d (2.0) |
| 37 | 22.7 | 0.86 d (7.0) |
| 38 | 10.9 | 0.72 d (7.0) |
| 39 | 12.6 | 1.63 s |
| 40 | 18.4 | 0.88 d (6.5) |

TABLE 8-continued

| Pos.[a] | $\delta_C$ | $\delta_H$ Mult. (J in Hz) |
|---|---|---|
| 41 | 12.0 | 1.59 s |
| 42 | 10.1 | 0.91 d (7.0) |
| 43 | 53.4 | 4.17 m |
| 44 | | 7.40 d (9.5) |
| 46 | 47.2 | 2.51 m |
| 47 | 73.9 | 3.52 m |
| 48 | 33.0 | 1.46 m |
| 49 | 29.9 | 1.28 m |
| 50 | 36.2 | 1.55 m |
| 51 | 83.1 | 3.54 m |
| 53 | 130.4 | 5.49 d (10.0) |
| 54 | 35.3 | 2.67 m |
| 55 | 74.6 | 3.76 m |
| 56 | 53.6 | 4.07 m |
| 57 | | 7.57 d (10.5) |
| 59 | 124.5 | 6.36 d (15.5) |
| 60 | 146.6 | 6.87 d (15.5) |
| 63 | 44.5 | 3.20 dq (10.0, 7.0) |
| 64 | 77.2 | 4.04 m |
| 67 | 73.8 | 5.00 pent (6.0) |
| 68 | 17.9 | 1.23 d (6.0) |
| 69 | 15.2 | 1.11 d (7.0) |
| 70 | 16.0 | 0.95 d (6.5) |
| 71 | 11.7 | 1.48 s |
| 72 | 18.1 | 0.99 d (7.0) |
| 73 | 75.7 | 3.60 m |
| 74 | 31.5 | 1.48 m |
| 75 | 19.5 | 0.87 d (7.0) |
| 76 | 20.1 | 0.93 d (7.0) |
| 77 | 23.8 | 1.20 s |
| 78 | 23.7 | 1.26 s |
| 79 | 15.3 | 0.76 d (7.0) |
| 80 | 17.7 | 1.10 s |
| 81 | 25.2 | 1.17 s |
| 2' | 68.8 | 4.52 dd (7.5, 5.0) |
| 3' | 40.2 | 2.78 m, 2.82 m |
| 36-OCH$_3$ | 52.6 | 3.73 s |
| 66-OCH$_3$ | 51.7 | 3.62 s |
| 1'-OCH$_3$ | 51.8 | 3.66 s |

[a] Only protonated carbons could be assigned from an HSQC experiment.

Example 11

This example demonstrates a method of obtaining an exemplary compound of the present invention.

A 2.0 mg solution of chondropsin A dimethyl ester in pyridine-$d_5$ was treated as described in Example 9 to give 0.8 mg of chondropsin D dimethyl ester. The FABMS, HPLC retention time and co-injection, and $^1$H NMR data were identical to those exhibited by the product obtained in Example 10.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of killing or selectively inhibiting the growth of leukemia cells, in a patient in need thereof, said method comprising administering to the patient an effective amount of at least one compound of formula (I)

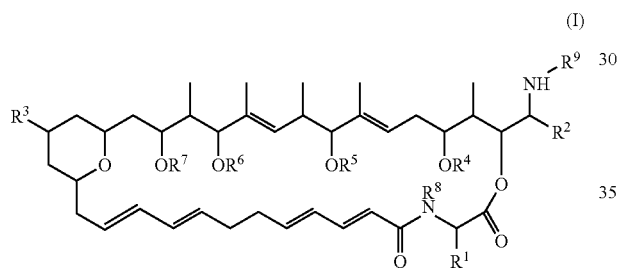

wherein:
$R^1$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof, wherein $R^1$ is unsubstituted or substituted with one or more substituents, which are the same or different, selected from the group consisting of oxo (=O), $OR^{1a}$, $CO_2R^{1a}$ and $OC(O)R^{1a}$, wherein $R^{1a}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof;

$R^2$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof, wherein $R^2$ is unsubstituted or substituted with one or more substituents, which are the same or different, selected from the group consisting of oxo (=O), $OR^{2a}$, or $OC(O)R^{2a}$, wherein $R^{2a}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof;

$R^3$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof;

$R^4$-$R^8$ are the same or different and each is $R^{10}$, $C(O)R^{10}$ or $SO_2R^{10}$, wherein $R^{10}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof, wherein $R^{10}$ is unsubstituted or substituted with one or more substituents, which are the same or different, selected from the group consisting of oxo (=O), $OR^{10a}$, $CO_2R^{10a}$, and $OC(O)R^{10a}$, wherein $R^{10a}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof, and $R^9$ is

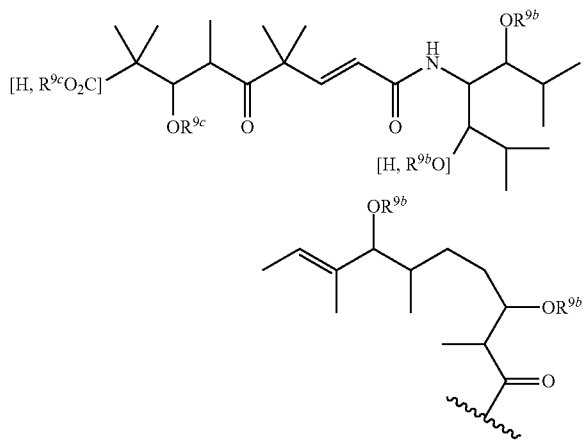

$R^{9a}$, $C(O)R^{9a}$ or $SO_2R^{9a}$, wherein $R^{9a}$ is a straight-chain or branched $C_{1-30}$ saturated alkyl, a straight-chain or branched $C_{2-30}$ unsaturated alkyl, or an aryl comprising 6-10 carbon atoms in the ring skeleton thereof, wherein $R^{9a}$ is unsubstituted or substituted with one or more substituents, which are the same or different, selected from the group consisting of oxo (=O), $OR^{9b}$, $OC(O)R^{9b}$, $OSO_2R^{9b}$, $NHR^{9b}$, $NHC(O)R^{9b}$ and $NHSO_2R^{9b}$, wherein $R^{9b}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof, wherein $R^{9b}$ is unsubstituted or substituted with one or more substituents, which are the same or different, selected from the group consisting of oxo (=O), $OR^{9c}$, $CO_2R^{9c}$, and $OC(O)R^{9c}$, wherein $R^{9c}$ is H, a straight-chain or branched $C_{1-30}$ saturated alkyl, a straight-chain or branched $C_{2-30}$ unsaturated alkyl, or an aryl comprising 6-10 carbon atoms in the ring skeleton thereof;

wherein $R^{1a}$, $R^{2a}$, $R^{10a}$ and $R^{9c}$ are unsubstituted or substituted with one or more substituents selected from the group consisting of halogen, amino, hydroxyl, oxo (=O), thio, cyano and nitro;

or a pharmaceutically acceptable salt thereof;

whereupon the leukemia cells are killed or their growth is selectively inhibited.

2. The method of claim 1, wherein said method further comprises administering an effective amount of at least one additional compound selected from the group consisting of bafilomycins, concanamycins, and benzolactone enamides.

3. The method of claim 1, wherein $R^1$ is $CHOHCO_2R^{1a}$, wherein $R^{1a}$ is H or methyl;
$R^2$ is $CHOHCH_3$;
$R^3$ is H or methyl;
$R^4$ is H or $C(O)CH_2CHOHCO_2R^{10}$;
$R^5$-$R^8$ are the same or different and each is H or $C(O)R^{10}$;
each $R^{10}$ is independently H or methyl; and $R^9$ is

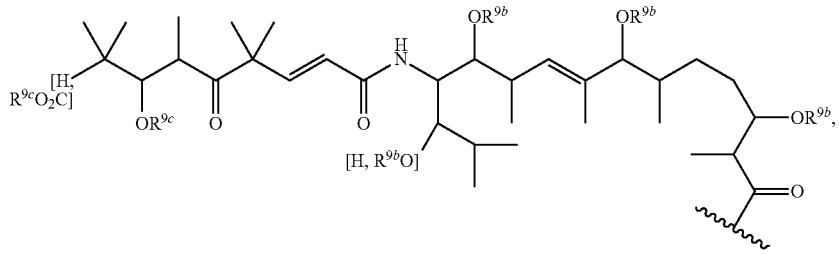

wherein $R^{9b}$ is H and $R^{9c}$ is H or methyl.

4. The method of claim 3, wherein said method further comprises administering an effective amount of at least one additional compound selected from the group consisting of bafilomycins, concanamycins, and benzolactone enamides.

5. The method of claim 3, wherein $R^5$-$R^8$ are all H and $R^9$ is

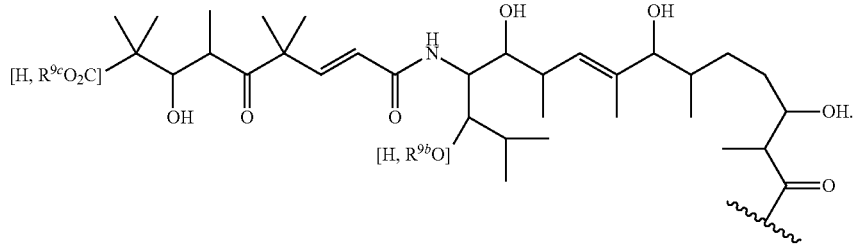

6. The method of claim 5, wherein said method further comprises administering an effective amount of at least one additional compound selected from the group consisting of bafilomycins, concanamycins, and benzolactone enamides.

7. The method of claim 5, wherein $R^{1a}$ is H; $R^3$ is methyl; $R^4$ is $C(O)CH_2CHOHCO_2R^{10}$; $R^{10}$ is H; the substituent labeled [H, $OR^{9b}$] is $OR^{9b}$; $R^{9b}$ is H; the substituent labeled [H, $CO_2R^{9c}$] is $CO_2R^{9c}$; and $R^{9c}$ is methyl.

8. The method of claim 7, wherein said method further comprises administering an effective amount of at least one additional compound selected from the group consisting of bafilomycins, concanamycins, and benzolactone enamides.

9. The method of claim 5, wherein $R^{1a}$ is H; $R^3$ is methyl; $R^4$ is H; the substituent labeled [H, $OR^{9b}$] is $OR^{9b}$; $R^{9b}$ is H; the substituent labeled [H, $CO_2R^{9c}$] is $CO_2R^{9c}$; and $R^{9c}$ is methyl.

10. The method of claim 9, wherein said method further comprises administering an effective amount of at least one additional compound selected from the group consisting of bafilomycins, concanamycins, and benzolactone enamides.

11. The method of claim 5, wherein $R^{1a}$ is methyl; $R^3$ is methyl; $R^4$ is $C(O)CH_2CHOHCO_2R^{10}$; $R^{10}$ is methyl; the substituent labeled [H, $OR^{9b}$] is $OR^{9b}$; $R^{9b}$ is H; the substituent labeled [H, $CO_2R^{9c}$] is $CO_2R^{9c}$; and $R^{9c}$ is methyl.

12. The method of claim 5, wherein $R^{1a}$ is H; $R^3$ is methyl; $R^4$ is $C(O)CH_2CHOHCO_2R^{10}$; $R^{10}$ is H; the substituent labeled [H, $OR^{9b}$] is H; the substituent labeled [H, $CO_2R^{9c}$] is $CO_2R^{9c}$; and $R^{9c}$ is methyl.

13. The method of claim 5, wherein $R^{1a}$ is methyl; $R^3$ is methyl; $R^4$ is $C(O)CH_2CHOHCO_2R^{10}$; $R^{10}$ is methyl; the substituent labeled [H, $OR^{9b}$] is H; the substituent labeled [H, $CO_2R^{9c}$] is $CO_2R^{9c}$; and $R^{9c}$ is methyl.

14. The method of claim 5, wherein $R^{1a}$ is H; $R^3$ is methyl; $R^4$ is $C(O)CH_2CHOHCO_2R^{10}$; $R^{10}$ is H; the substituent labeled [H, $OR^{9b}$] is H; and the substituent labeled [H, $CO_2R^{9c}$] is H.

15. The method of claim 5, wherein $R^{1a}$ is methyl; $R^3$ is methyl; $R^4$ is $C(O)CH_2CHOHCO_2R^{10}$; $R^{10}$ is methyl; the substituent labeled [H, $OR^{9b}$] is H; and the substituent labeled [H, $CO_2R^{9c}$] is H.

* * * * *